United States Patent
Youngblood et al.

(10) Patent No.: US 11,769,585 B2
(45) Date of Patent: Sep. 26, 2023

(54) HEALTH DATA EXCHANGE PLATFORM

(71) Applicant: Youngblood IP Holdings, LLC, Mooresville, NC (US)

(72) Inventors: Tara Youngblood, Mooresville, NC (US); Todd Youngblood, Mooresville, NC (US)

(73) Assignee: YOUNGBLOOD IP HOLDINGS, LLC, Mooresville, NC (US)

( * ) Notice: Subject to any disclaimer, the term of this patent is extended or adjusted under 35 U.S.C. 154(b) by 796 days.

(21) Appl. No.: 16/742,152

(22) Filed: Jan. 14, 2020

(65) Prior Publication Data

US 2020/0227160 A1 Jul. 16, 2020

Related U.S. Application Data

(60) Provisional application No. 62/792,572, filed on Jan. 15, 2019.

(51) Int. Cl.
| | | |
|---|---|---|
| *G16H 40/20* | (2018.01) | |
| *G16H 10/60* | (2018.01) | |
| *H04L 9/06* | (2006.01) | |
| *H04L 9/30* | (2006.01) | |
| *H04L 9/00* | (2022.01) | |

(52) U.S. Cl.
CPC ............. *G16H 40/20* (2018.01); *G16H 10/60* (2018.01); *H04L 9/0637* (2013.01); *H04L 9/30* (2013.01); *H04L 9/50* (2022.05); *H04L 2209/56* (2013.01)

(58) Field of Classification Search
CPC ...... G16H 40/20; G16H 10/60; H04L 9/0637; H04L 9/30; H04L 9/50
See application file for complete search history.

(56) References Cited

U.S. PATENT DOCUMENTS

| | | | |
|---|---|---|---|
| 6,978,931 | B2 | 12/2005 | Brobeck |
| 8,615,532 | B2 | 12/2013 | Bessette |
| 9,582,641 | B2 | 2/2017 | Rock |
| 9,792,658 | B1 * | 10/2017 | Vijendra ............... G06Q 50/01 |
| 2006/0229911 | A1 | 10/2006 | Gropper et al. |
| 2007/0027715 | A1 | 2/2007 | Gropper et al. |
| 2010/0082369 | A1 | 4/2010 | Prenelus et al. |
| 2014/0279722 | A1 * | 9/2014 | Singh .................. G06F 16/9535 |
| | | | 706/11 |
| 2014/0344015 | A1 | 11/2014 | Púertolas-Moñtanés et al. |

(Continued)

OTHER PUBLICATIONS

Peng Zhang et al. FHIRChain: Applying Blockchain to Securely and Scalably Share Clinical Data. Elsevier, Computational and Structural Biotechnology Journal, vol. 16, Jul. 29, 2018, pp. 267-278.

*Primary Examiner* — Mamon Obeid
*Assistant Examiner* — Chance L Smith
(74) *Attorney, Agent, or Firm* — NEO IP

(57) ABSTRACT

The present invention provides systems and methods for exchanging health data. A health data exchange platform includes health data from a plurality of data sources. The health data exchange platform preferably utilizes blockchain technology. The health data exchange platform includes both buyers of health data and suppliers of health data. The health data exchange platform includes a phenotype network system including at least one remote server, a user profile database, a report database, a permissions database, a geographic incident database, and a medical community database.

20 Claims, 18 Drawing Sheets

(56) References Cited

U.S. PATENT DOCUMENTS

| | | |
|---|---|---|
| 2015/0154646 A1 | 6/2015 | Mishra et al. |
| 2015/0317439 A1* | 11/2015 | Kress .................... G16H 40/20 705/2 |
| 2015/0332283 A1 | 11/2015 | Witchey |
| 2016/0283920 A1 | 9/2016 | Fisher et al. |
| 2017/0011460 A1 | 1/2017 | Molinari et al. |
| 2017/0019496 A1 | 1/2017 | Orbach |
| 2017/0024656 A1* | 1/2017 | Gilon .................... G16H 10/20 |
| 2017/0039330 A1 | 2/2017 | Tanner et al. |
| 2017/0316162 A1 | 11/2017 | Warner et al. |
| 2017/0358041 A1 | 12/2017 | Forbes, Jr. et al. |
| 2017/0364655 A1 | 12/2017 | Farooqi |
| 2018/0048461 A1 | 2/2018 | Jutla et al. |
| 2018/0060496 A1 | 3/2018 | Bulleit et al. |
| 2018/0082023 A1 | 3/2018 | Curbera et al. |
| 2018/0082291 A1 | 3/2018 | Allen et al. |
| 2018/0103042 A1 | 4/2018 | Castagna et al. |
| 2018/0165588 A1* | 6/2018 | Saxena .................. G06N 5/043 |
| 2018/0218779 A1 | 8/2018 | Collins, Jr. |
| 2018/0248981 A1 | 8/2018 | Salem |
| 2018/0253539 A1 | 9/2018 | Minter et al. |
| 2018/0254093 A1 | 9/2018 | Rose |
| 2018/0268930 A1 | 9/2018 | Lee |
| 2018/0294047 A1* | 10/2018 | Hosseini ................ G16B 50/30 |
| 2018/0323975 A1 | 11/2018 | Curbera et al. |
| 2018/0350451 A1* | 12/2018 | Ohnemus .............. H04L 67/535 |
| 2019/0139621 A1* | 5/2019 | Wang .................... G16B 45/00 |
| 2019/0311791 A1* | 10/2019 | St. Paul ................. G16H 10/60 |
| 2020/0035341 A1* | 1/2020 | Kain ...................... G16H 10/20 |
| 2022/0199208 A1* | 6/2022 | McFarlane ............. H04L 9/088 |

* cited by examiner

HEALTH DATA EXCHANGE PLATFORM

CROSS REFERENCE TO RELATED APPLICATIONS

This application claims priority from U.S. Provisional Patent Application No. 62/792,572, filed Jan. 15, 2019, which is incorporated herein by reference in its entirety.

BACKGROUND OF THE INVENTION

1. Field of the Invention

This invention relates broadly and generally to systems and methods for a health data exchange platform, and more particularly, health data aggregation, data formatting, digital contracts, micropayments, and data analytics.

2. Description of the Prior Art

Various methods of controlling and securing health data are known. Health data must be kept private and secure. A major challenge for storing health data is interoperability between data applications used within the industry by hospitals, doctors, patients, insurance companies, etc. Additionally, health data must be easily and quickly accessible by the hospitals, the doctors, the patients, the insurance companies, etc.

Prior art patent documents include the following:

U.S. Pat. No. 6,978,931 for energy credit card system by inventor Brobeck, filed Apr. 13, 2004 and issued Dec. 27, 2005, is directed to a method of providing an energy credit system for providing redeemable energy or mass transit credits to consumers who contribute power to a shared electric power grid wherein the excess power generated by each consumer to the power grid is measured and energy credits are awarded to those consumers who contribute power to the power grid. Each consumer receiving energy credits is allowed to redeem those credits by acquiring fuel, power or mass transit tickets. A separate energy brokerage house is provided which receives compensation from the operator of the power grid for power provided to the grid by the consumers and compensates the fuel or energy provider or mass transit system for the energy credits redeemed by each consumer. The operator of the power grid compensates the providers of fuel, energy or mass transit directly for the redeemed energy credits.

U. S. Publication No. 20060229911 for personal control of healthcare information and related systems, methods, and devices by inventors Gropper et al., filed Feb. 10, 2006 and published Oct. 12, 2006, is directed to a healthcare information system including: a client interface unit for creating one or more healthcare information documents, a repository in communication with the client interface unit for storing one or more healthcare information documents received from the client interface unit, a registry in communication with the repository for maintaining an index table of one or more healthcare information documents stored in the repository and for maintaining control information associated with each document for controlling the distribution of each documents from the repository, and a patient interface unit in communication with the registry for enabling a patient to configure at least a portion of the control information within the registry associated with one or more healthcare information documents.

U. S. Publication No. 20070027715 for private health information interchange and related systems, methods, and devices by inventors Gropper et al., filed Jun. 13, 2006 and published Feb. 1, 2007, is directed to a healthcare information interchange system including a sender for originating one or more healthcare information documents associated with a patient, a first repository in communication with the sender for i) storing the one or more healthcare information documents received from the sender and ii) distributing the one or more healthcare information documents based on consent rules associated with each of the one or more documents, a recipient for receiving the one or more healthcare information documents based on the consent rules, and an identity provider for assigning first and second identities to the patient, the first identity being presented to the first repository by the sender to identify the patient, the second identity being presented by the first repository to the recipient to identify the patient.

U.S. Publication No. 20100082369 for systems and methods for interconnected personalized digital health services by inventors Prenelus et al., filed Sep. 29, 2008 and published Apr. 1, 2010, is directed to systems and methods for providing personalized, interconnected digital health services. A digital health services system includes an access portal providing access to health information for a patient from a plurality of clinical data sources. The system also includes a shared registry and repository storing information from the plurality of clinical data sources for interconnection and access via the access portal. The system further includes digital health information and services generating a personalized care plan for the patient based on health information from the shared registry and repository in conjunction with one or more rules applied to the health information to match the care plan with the health information for the patient and to track patient outcomes based upon compliance with the recommended care plan.

U.S. Pat. No. 8,615,532 for system and method for electronically managing medical data files by inventor Bessette, filed Sep. 27, 2012 and issued Dec. 24, 2013, is directed to a network server arrangement including a processor with a machine readable storage encoded with software for execution by the processor. The network server arrangement is responsive to requests to access a medical record of an individual and generates summary medical record data including summary information having a plurality of data elements associated with the individual, at least one of the data elements conveying medical information about the individual, and a pointers component including at least one pointer pointing to a network location containing importable medical information in connection with the individual that is not contained in the summary information component. The pointer includes a machine readable address part for processing by the client, allowing the client to import the medical information from the network location, and a label part for displaying to a user the nature of the medical information residing at the network location.

U. S. Publication No. 20140279722 for methods and system for inferring user attributes in a social networking system by inventors Singh et al., filed Mar. 15, 2013 and published Sep. 18, 2014, is directed to method and system for inferring user attributes in a social networking system. The method includes maintaining a social graph comprising a plurality of nodes and a plurality of edges between the nodes. An unknown, incomplete, or inaccurate user attribute for a user is identified, and a plurality of probability lists are generated using a corresponding plurality of probability algorithms that utilize known user attributes and the social graph. The probability lists include a set of probability entries, each including a prediction we value for the unknown, incomplete, or inaccurate user attribute and a confidence score. Using the probability lists and a plurality of weights corresponding to the probability algorithms, an inferred user attribute value is generated and stored. The weights may be adjusted based upon learning the correct value of the unknown, incomplete, or inaccurate user attribute, and search results may be modified to include the user for search queries seeking information about the inferred user attribute.

U. S. Publication No. 20140344015 for systems and methods enabling consumers to control and monetize their personal data by inventors Puértolas-Montañés et al., filed May 20, 2014 and published Nov. 20, 2014, is directed to systems and methods for providing personal computing and service provider platforms for enabling a consumer to control and monetize their personal data while managing their online privacy. Business methods utilizing the systems and methods resemble those of profit-sharing and asset-sharing paradigms such as cooperatives, and they comprise means for enabling a diverse array of individual subscriber shareholders to receive dividends, share profits and assets, pool resources, and otherwise participate in the ownership of the personal and behavioral data and other content that they generate.

U. S. Publication No. 20150332283 for healthcare transaction validation via blockchain proof-of-work, systems and methods by inventor Witchey, filed May 13, 2015 and published Nov. 19, 2015, is directed to healthcare transaction validation systems and methods. Healthcare transactions associated with a stakeholder are compiled into a chain of healthcare transaction blocks. The chain can be considered a chronicle of person's healthcare path through life. When a transaction is conducted, the corresponding healthcare parameters (e.g., inputs, outputs, clinical evidence, outcomes, etc.) are sent to one or more validation devices. The devices establish a validity of the transaction and generate a new block via a proof-of-work principle. Once the new block has been calculated it can be appended to the stakeholder's health care blockchain.

U. S. Publication No. 20160283920 for authentication and verification of digital data utilizing blockchain technology by inventors Fisher et al., filed Mar. 28, 2016 and published Sep. 29, 2016, is directed to a method for authenticating a chain of custody utilizing blockchain technology, whereby digital evidence or other digital content is acquired and then hashed to produce a hash fingerprint/signature and then immediately or instantly submitting said hash fingerprint/signature to the blockchain using the blockchain network protocol, forming an immediate verifiable chain of custody without human interaction or requiring a trusted third party.

U.S. Publication No. 20170011460 for systems and methods for trading, clearing and settling securities transactions using blockchain technology by inventors Molinari et al., filed Jun. 30, 2016 and published Jan. 12, 2017, is directed to a securities trading system that utilizes a distributed blockchain ledger to conduct security transactions. Users are provided with cryptographic wallets that enable the users to access a peer-to-peer network of computing nodes on which the distributed blockchain ledger is managed. The securities made available through the network may be stored directly on the blockchain ledger itself. Smart contracts may be utilized to transfer the securities among the users and to verify that all transactions are in compliance with applicable regulatory rules and other restrictions.

U.S. Publication No. 20170019496 for needs-matching navigator system by inventor Orbach, filed Jul. 14, 2015 and published Jan. 19, 2017, is directed to a needs-matching navigator system and social network facilitator appurtenances including, for a large user plurality, software driven modules residing on electronic communications enabled platforms and devices. Beyond altruistically enhancing flourishing life horizons and life quality metrics, the modules facilitate (A) knowing respective user bias, profile, perspective, wellbeing orientation, and privacy preference; (B) understanding user needs description and wellbeing criteria; (C) finding answer and solutions to the needs by user biased projecting the description onto electronically stored knowledge-bases; (D) matching the user to the answers and solutions; and preferably (E) creating an instant electronic communications interactive community for the respective user, by inverse projecting large subsets of the answers and solutions back onto the large plurality of users; according to said users' profiles and needs descriptions. This navigable community may be classified into spontaneous castes; having various degrees of relevant understanding, expertise, experience, and/or curiosity about these answer and/or solution projections.

U. S. Publication No. 20170039330 for system and method for decentralized autonomous healthcare economy platform by inventors Tanner et al., filed Nov. 5, 2015 and published Feb. 9, 2017, is directed to a system and method for a decentralized autonomous healthcare economy platform. The system and method aggregates all of the healthcare data into a global graph-theoretic topology and processes the data via a hybrid federated and peer to peer distributed processing architectures.

U.S. Pat. No. 9,582,641 for distributed healthcare database system and method by inventor Rock, filed Mar. 25, 2014 and issued Feb. 28, 2017, is directed to a system and method distributing healthcare database access. The system and method interpose a data mapping server (DMS) between a data request user server (DRS) and data service user server (DSS) to manage data transfers between the DSS and the DRS such that disparate database characteristics of the DRS/DSS are accommodated in real-time and permit asynchronous healthcare activity to be triggered. The DMS operates with a data access matrix (DAM) having each referenced DRS/DSS intersection pair associated with read/write control processes (RWP) that include read data (RDD) and write data (WRD) processes to permit data access across the disparate DRS/DSS database boundaries. The DAM may have multiple dimensions to accommodate asynchronously activated process threads within an overall patient healthcare plan (PHP) that operate to trigger healthcare provider alarms and other activity associated with the transfer/update of data between the DSS and the DRS.

U. S. Publication No. 20170316162 for distributed systems for secure storage and retrieval of encrypted biological specimen data by inventors Warner et al., filed Jul. 17, 2017 and published Nov. 2, 2017, is directed to distributed systems for secure storage and retrieval of encrypted biological specimen data. The system may comprise a submission device client operable to send, to a patient record server device, a patient record; and receive, from the patient record server device, a confirmation of receipt of the patient record. The system may further comprise a patient record server device comprising a first processor and second memory, a second communications interface associated with the first processor and second memory and operable to receive, from the submission device client, the patient record; send, to the submission device client, the confirmation of receipt of the patient record; receive, from a member device client, patient profile information; determine search results based on the patient profile information; and send, to the member device client, information indicating the search results. The system may yet further comprise a member device client operable to send, to the patient record server device, the patient profile information; receive, from the patient record server device, the information indicating the search results based on the patient profile information; and receive the search results based on the information indicating the search results.

U. S. Publication No. 20170358041 for systems and methods for advanced energy settlements, network-based messaging, and applications supporting the same on a blockchain platform by inventors Forbes et al., filed Aug. 7, 2017 and published Dec. 14, 2017, is directed to systems and methods for financial settlement of transactions within an electric power grid network. A multiplicity of active grid elements are constructed and configured for electric connection and network-based communication over a blockchain-based platform. The multiplicity of active grid elements are operable to make peer-to-peer transactions based on their participation within the electric power grid by generating and executing a digital contract. The multiplicity of active grid elements generate messages autonomously and/or automatically within a predetermined time interval. The messages comprise energy related data and settlement related data. The energy related data of the multiplicity of active grid elements are based on measurement and verification. The energy related data and the settlement related data are validated and recorded on a distributed ledger with a time stamp and a geodetic reference.

U. S. Publication No. 20170364655 for monitoring adherence to a healthcare plan by inventor Farooqi, filed Jun. 15, 2017 and published Dec. 21, 2017, is directed to a healthcare adherence monitoring system (HAMS) that can be used to monitor adherence of a healthcare recipient to a healthcare plan (e.g., a medication, exercise, and nutrition regimen). The HAMS may receive a personalized prescription including one or more pre-coded prescription components and/or customized recommendations of the healthcare plan from a healthcare provider device via a communication network. The HAMS may then incorporate the received personalized prescription for the healthcare recipient into a healthcare mobile application that a healthcare recipient device can access via the communication network. The HAMS may further dynamically update the personalized prescription based on configuration parameters received from the healthcare mobile application on the healthcare recipient device via the communication network and communicate with the healthcare mobile application on the healthcare recipient device via the communication network to monitor the healthcare recipient's adherence to the dynamically updated personalized prescription.

U. S. Publication No. 20180048461 for apparatus, system, and methods for a blockchain identity translator by inventors Jutla et al., filed Aug. 9, 2017 and published Feb. 15, 2018, is directed to blockchain applications that can generate public/private key pairs without knowing the true identity of the owner of the private key. Many applications, such as in healthcare or corporate banking, require known identities for legal or regulatory reasons. Therefore a mapping between PKI certificate credentials maintained by certificate authorities and blockchain credentials is needed as one means of transferring real-world identity to blockchain applications. A method and system are provided to associate a PKI certificate to one or more accounts in a cryptographic wallet and extend the due diligence of a third-party certificate authority for identity management on blockchains.

U. S. Publication No. 20180060496 for blockchain-based mechanisms for secure health information resource exchange by inventors Bulleit et al., filed Aug. 23, 2017 and published Mar. 1, 2018, is directed to technologies to secure flexible access to the healthcare information resources (HIR) contained within electronic health records (EHR) systems. By managing access permissions with certified self-sovereign identities and distributed ledger techniques, HIR may be secured. Patients and other users may be registered to access a distributed ledger, such as a healthcare blockchain, employed to set, host and adjudicate permissions to access HIR. Authorized owners and/or patients with rights to their own HIR may be able to grant fine-grained and conditional access permissions to third-parties. Information transfers and transactions occurring according to these permissions may be logged within smart contracts incorporated in the healthcare blockchain.

U. S. Publication No. 20180082023 for secure distributed patient consent and information management by inventors Curbera et al., filed Aug. 9, 2017 and published Mar. 22, 2018, is directed to mechanisms to implement secure distributed patient consent and patient information management that addresses the competing needs for efficient access to electronic medical records by authorized parties while maintaining protection of privacy of patient health related information and complying with governing regulations. The mechanisms implement a tamper-proof and immutable ledger storage system to manage patient consent information and distribution of patient information based on the patient consent information. The ledger storage system operates in conjunction with a master patient record index (MPRI) component to enable the exchange of patient information among health providers once consent has been granted by the patient. Once provided with a record locator from the MPRI, a health provider can directly request patient information from another health provider, where the patient information resides as indicated by the record locator, or an intermediary data hub implementation may be utilized.

U. S. Publication No. 20180082291 for systems and methods that utilize blockchain digital certificates for data transactions by inventors Allen et al., filed Oct. 18, 2017 and published Mar. 22, 2018, is directed to systems and methods that use blockchain digital certificates are described herein. One example of a system includes generating a digital certificate including transaction data for a transaction, creating a blockchain blob of the transaction data, generating an electronic ownership token for the digital certificate, and transferring the electronic ownership token to an owner of the digital certificate.

U. S. Publication No. 20180103042 for automated data authentication and service authorization via cryptographic keys in a private blockchain by inventors Castagna et al., filed Oct. 12, 2016 and published Apr. 12, 2018, is directed to a system for authenticating records belonging to an individual or entity and providing authorized access of said records to service providers. The invention utilizes a private blockchain to store various types of records to be conveyed to the service providers. In this way, the individual or entity may securely store on the blockchain all records relevant to service providers, then provide the service providers with secured access to said records such that the providers may access only the specific records for which they are authorized, e.g. a healthcare provider may access only the healthcare records on the blockchain.

U. S. Publication No. 20180165588 for providing healthcare-related, blockchain-associated cognitive insights using blockchains by inventors Saxena et al., filed Dec. 9, 2016 and published Jun. 14, 2018, is directed to a method, system and computer-usable medium for providing cognitive insights comprising receiving data from a plurality of data sources, at least some of the plurality of data sources comprising healthcare related data sources and blockchain data sources; processing the data from the plurality of data sources to provide a healthcare-related, blockchain-associated cognitive insight; and, providing the healthcare-related, blockchain-associated cognitive insight to a destination.

U. S. Publication No. 20180218779 for verification of clinical data by inventor Collins, filed Jan. 22, 2018 and published Aug. 2, 2018, is directed to a method for securely storing clinical data associated with a clinical trial in a data store including receiving the clinical data from a user, forming a value representing the clinical data including applying a one-way function to the clinical data, storing the value in a distributed ledger, and storing the clinical data in the data store.

U. S. Publication No. 20180248981 for enhanced personal care system employing blockchain functionality by inventor Salem, filed Apr. 2, 2018 and published Aug. 30, 2018, is directed to an apparatus including a personal care display device having connection ports and a remote central server device arrangement. The personal care display device is configured to transmit user healthcare communications personalized to the user and receive user healthcare communications personalized to the user from the remote central server device arrangement, for the user to freely substitute selected and different hardware personal care modules in the plurality of connection ports, and to maintain an interactive diary for the user. One hardware personal care module includes a healthcare personal care module used with the personal care display device to assess user healthcare needs and provide healthcare information and recommendations specifically for the user. The remote central server device arrangement provides disease points to users for use in exchange for goods and services and health points (HPs) for quantified healthy behavior that a user can redeem with available providers.

U. S. Publication No. 20180253539 for robust system and method of authenticating a client in non-face-to-face online interactions based on a combination of live biometrics, biographical data, blockchain transactions and signed digital certificates by inventors Minter et al., filed Mar. 5, 2017 and published Sep. 6, 2018, is directed to a system, method and computer-readable medium for authenticating the identity of a client in non-face-to-face transactions. At the core of the invention is the creation and use of live distributed ledger Biometric and Biographical Blockchain Databases, the use of live biometrics and the use of prior art Public Key digital certificate technology. The client data in the Blockchain is dynamically updated and digitally signed each time new live samples are captured. The Blockchains serve as a permanent history of the client's biometric or biographical transactions that can be used to create a completely traceable audit trail. Data used for authentication may also originate from a Secure Computing Device such as a computer server that is registered by an accredited authority, has its own digitally signed embedded registration certificate, is equipped with a hardware security module (HSM) capable of safeguarding cryptographic keys and performing standard crypto-processing functions and has embedded authorized users digitally signed public key certificates and biometric authentication certificates. Client data is collected from various authoritative sources and processed by a Data Analytics Authentication Processor (DAAP) to generate the client's Service Access Authentication Tag (SAAT) score and a client-specific profile that determines the client's precise eligibility and entitlement to services offered by a plurality of online services providers.

U. S. Publication No. 20180254093 for cryptographically secure medical test data distribution system using smart testing/diagnostic devices by inventor Rose, filed Mar. 2, 2018 and published Sep. 6, 2018, is directed to a diagnostic device is provided that obtains test results and transmits a cryptographically secure version of such test results. The diagnostic device may be provisioned with a unique first public key and first private key pair and a unique device identifier for the diagnostic device. A link may be established with a mobile communication device associated with a unique patient identifier. A test request may be received from the mobile communication device including the patient identifier. The diagnostic device may then verify whether the requested test can or should be performed based, at least partially, on the patient identifier. If the patient identifier is verified, the diagnostic device may perform the requested test to obtain a test result. The test result may be encrypt/signed using the first private key and a first authorized receiver public key to obtain a first encrypted result that is transmitted to the mobile communication device.

U. S. Publication No. 20180268930 for method for building cloud-based medical image database for protection of patient information and reading medical image therefrom by inventor Lee, filed Oct. 26, 2016 and published Sep. 20, 2018, is directed to a method for building a cloud-based medical image database for the protection of patient information. A method for building a cloud-based medical image database and reading a medical image therefrom includes a acquiring a medical image of a patient by a medical device; separating patient information data from medical information data in the medical image; encrypting the patient information data using a block chain technique; separately transmitting the encrypted patient information data and the medical information data to a cloud database and storing the same in the cloud database; decrypting the encrypted patient information data stored in the cloud database, using the block chain technique; and reading the medical image to perform diagnosis and consulting for the patient.

U. S. Publication No. 20180323975 for creating match cohorts and exchanging protecting data using blockchain by inventors Curbera, filed May 4, 2017 and published Nov. 8, 2018, is directed to a method, computing system and computer program product. A first entity system that stores sensitive information associated with different entities applies a hash function a portion of the sensitive information to produce hash values. Transaction information pertaining to transactions performed on entity systems are stored within a blockchain database accessible to the entity systems. The transaction information includes hash values corresponding to associated entities from the entity systems. The hash values of the first entity system are compared to the hash values from others of the entity systems to determine entity systems containing information pertaining to same entities. The sensitive information for an entity of the first entity system is exchanged with the determined entity systems containing information for that entity.

U. S. Publication No. 20180350451 for automated health data acquisition, processing and communication system and method by inventors Ohnemus et al., filed Nov. 23, 2016 and published Dec. 6, 2018, is directed to a system and method to classify user activity. A passive tracking device, a processor configured to receive information from the tracking device, and a database are disclosed, in which the database is accessible by the processor and stores tracking device information, user profile information and external information. The processor is configured to execute instructions that cause the processor to perform various steps, such as to define a first activity unit having a first start time that corresponds to detection of the user being engaged in an activity, and monitor the tracking device information, the external information or both. The processor is further configured to establish a first end time of the first activity unit using the monitored information, and automatically ascribe a classification of the first activity unit. The classification of the first activity unit is output to a display of a computing device, and the classification of the first activity unit is stored in the database. Moreover, a user interface is provided that includes selectable options associated with the first activity unit. Thereafter, in response to at least a received selection of at least one of the selectable options, the classification is revised by: joining the first activity unit and a second activity unit having a second start time and a second end time, such that the revised classification has a start time equal to the first start time and an end time equal to the second end time. Further, the first activity unit is merged with a second activity unit having a second start time and a second end time, such that the revised classification has a start time equal to the first start time and an end time equal to the second end time. Alternatively, the first activity unit is divided into at least two activity units, each of at least two activity units having a different respective start time and a different respective end time. The revised classification is output to a display of a computing device, the revised classification is stored in the database.

SUMMARY OF THE INVENTION

The present invention relates broadly and generally to systems and methods for a health data exchange platform, and more particularly, health data aggregation, data formatting, digital contracts, micropayments, and data analytics.

In one embodiment, the present invention provides a system for exchanging health data including a phenotype network that includes at least one user device and at least one remote server in network communication with a health data exchange platform, wherein the at least one remote server includes a phenotype database, a report database, a recommendation database, and a permissions database, wherein the report database includes health data, wherein the at least one user device is operable to authorize sharing of selected health data to a third-party device via a graphical user interface (GUI), thereby creating selected permissible data, wherein the health data exchange platform is operable to exchange the selected permissible data with the third-party device, wherein the phenotype network includes a plurality of user nodes, a plurality of phenotype or concept nodes, and a plurality of edges connecting the plurality of user nodes and/or the phenotype or concept nodes, and wherein the phenotype network is operable to automatically suggest a connection with another user, at least one phenotype, at least one medical entity, and/or at least one health status.

In another embodiment, the present invention provides a system for exchanging health data including a phenotype network that includes at least one user device and at least one remote server in network communication with a health data exchange platform, wherein the at least one remote server includes a phenotype database, a report database, a recommendation database, and a permissions database, wherein the report database includes health data, wherein the at least one user device is operable to authorize sharing of selected health data to a third-party device via a graphical user interface (GUI), thereby creating selected permissible data, wherein the health data exchange platform is operable to exchange the selected permissible data with the third-party device, wherein the phenotype network includes a plurality of user nodes, a plurality of phenotype or concept nodes, and a plurality of edges connecting the plurality of user nodes and/or the phenotype or concept nodes, wherein the phenotype network is operable to automatically suggest a connection with another user, at least one phenotype, at least one medical entity, and/or at least one health status, wherein the at least one remote server includes a plurality of distributed servers, wherein the health data exchange platform includes a distributed ledger, and wherein the health data exchange platform uses a private key and a public key to encrypt data stored on the distributed ledger.

In yet another embodiment, the present invention provides a system for exchanging health data including a phenotype network that includes at least one user device and at least one remote server in network communication with a health data exchange platform, wherein the at least one remote server includes a phenotype database, a report database, a recommendation database, and a permissions database, wherein the report database includes health data, wherein the at least one user device is operable to authorize sharing of selected health data to a third-party device via a graphical user interface (GUI), thereby creating selected permissible data, wherein the health data exchange platform is operable to exchange the selected permissible data with the third-party device, wherein the health data exchange platform is operable to process a micropayment between the at least one user device and the third-party device, wherein the phenotype network includes a plurality of user nodes, a plurality of phenotype or concept nodes, and a plurality of edges connecting the plurality of user nodes and/or the phenotype or concept nodes, wherein the phenotype network is operable to automatically suggest a connection with another user, at least one phenotype, at least one medical entity, and/or at least one health status, wherein the at least one remote server includes a plurality of distributed servers, wherein the health data exchange platform includes a distributed ledger, wherein the health data exchange platform uses a private key and a public key to encrypt data stored on the distributed ledger, and wherein the permissions database stores links to one or more locations where the selected permissible data is stored on the distributed ledger.

These and other aspects of the present invention will become apparent to those skilled in the art after a reading of the following description of the preferred embodiment when considered with the drawings, as they support the claimed invention.

DETAILED DESCRIPTION

Figure 1:
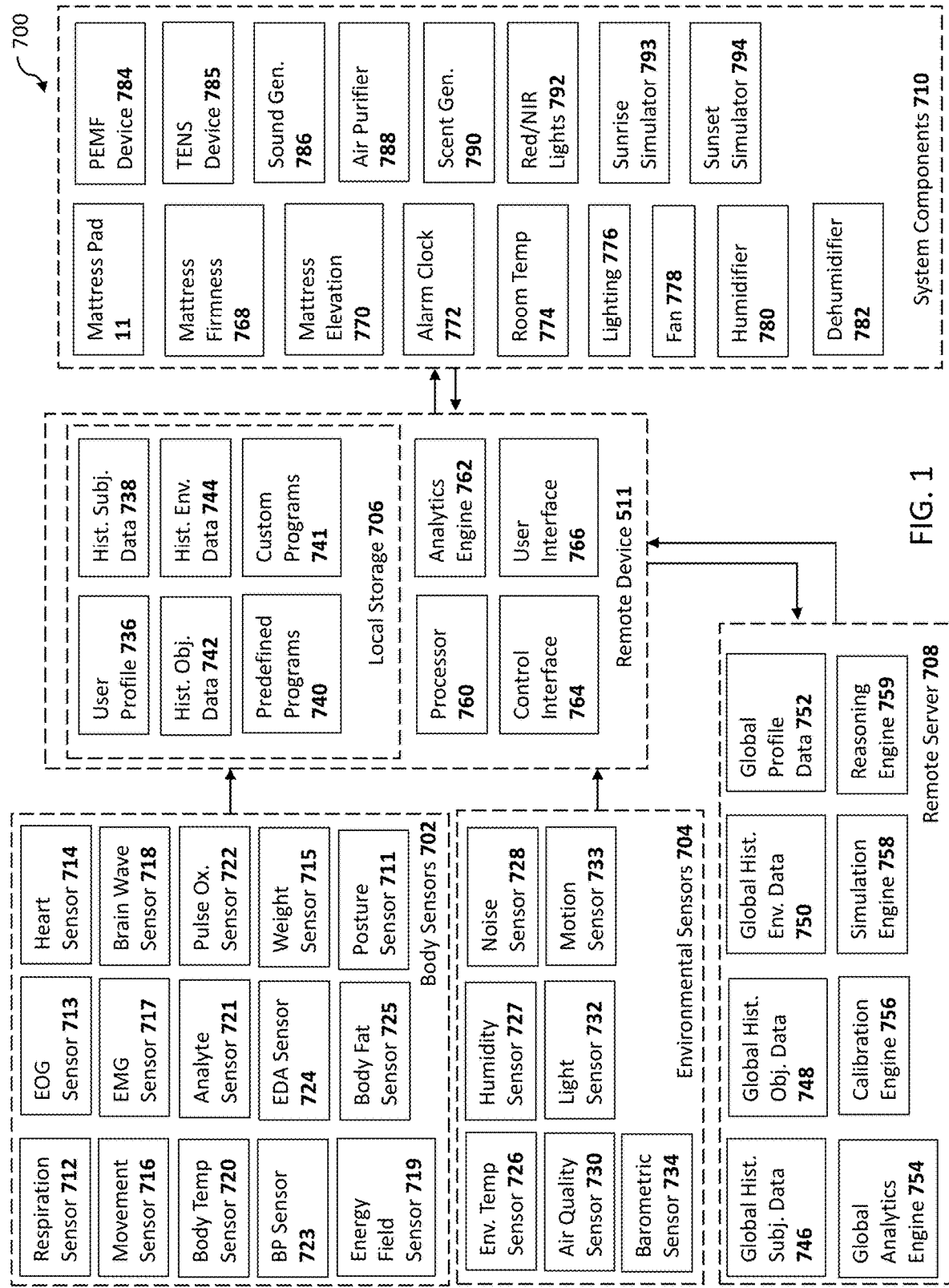
FIG. 1 is a block diagram of one embodiment of a stress reduction and sleep promotion system.

The present invention relates broadly and generally to systems and methods for a health data exchange platform, and more particularly, health data aggregation, data formatting, digital contracts, micropayments, and data analytics.

In one embodiment, the present invention provides a system for exchanging health data including a phenotype network that includes at least one user device and at least one remote server in network communication with a health data exchange platform, wherein the at least one remote server includes a phenotype database, a report database, a recommendation database, and a permissions database, wherein the report database includes health data, wherein the at least one user device is operable to authorize sharing of selected health data to a third-party device via a graphical user interface (GUI), thereby creating selected permissible data, wherein the health data exchange platform is operable to exchange the selected permissible data with the third-party device, wherein the phenotype network includes a plurality of user nodes, a plurality of phenotype or concept nodes, and a plurality of edges connecting the plurality of user nodes and/or the phenotype or concept nodes, and wherein the phenotype network is operable to automatically suggest a connection with another user, at least one phenotype, at least one medical entity, and/or at least one health status.

In another embodiment, the present invention provides a system for exchanging health data including a phenotype network that includes at least one user device and at least one remote server in network communication with a health data exchange platform, wherein the at least one remote server includes a phenotype database, a report database, a recommendation database, and a permissions database, wherein the report database includes health data, wherein the at least one user device is operable to authorize sharing of selected health data to a third-party device via a graphical user interface (GUI), thereby creating selected permissible data, wherein the health data exchange platform is operable to exchange the selected permissible data with the third-party device, wherein the phenotype network includes a plurality of user nodes, a plurality of phenotype or concept nodes, and a plurality of edges connecting the plurality of user nodes and/or the phenotype or concept nodes, wherein the phenotype network is operable to automatically suggest a connection with another user, at least one phenotype, at least one medical entity, and/or at least one health status, wherein the at least one remote server includes a plurality of distributed servers, wherein the health data exchange platform includes a distributed ledger, and wherein the health data exchange platform uses a private key and a public key to encrypt data stored on the distributed ledger.

In yet another embodiment, the present invention provides a system for exchanging health data including a phenotype network that includes at least one user device and at least one remote server in network communication with a health data exchange platform, wherein the at least one remote server includes a phenotype database, a report database, a recommendation database, and a permissions database, wherein the report database includes health data, wherein the at least one user device is operable to authorize sharing of selected health data to a third-party device via a graphical user interface (GUI), thereby creating selected permissible data, wherein the health data exchange platform is operable to exchange the selected permissible data with the third-party device, wherein the health data exchange platform is operable to process a micropayment between the at least one user device and the third-party device, wherein the phenotype network includes a plurality of user nodes, a plurality of phenotype or concept nodes, and a plurality of edges connecting the plurality of user nodes and/or the phenotype or concept nodes, wherein the phenotype network is operable to automatically suggest a connection with another user, at least one phenotype, at least one medical entity, and/or at least one health status, wherein the at least one remote server includes a plurality of distributed servers, wherein the health data exchange platform includes a distributed ledger, wherein the health data exchange platform uses a private key and a public key to encrypt data stored on the distributed ledger, and wherein the permissions database stores links to one or more locations where the selected permissible data is stored on the distributed ledger.

Referring now to the drawings in general, the illustrations are for the purpose of describing a preferred embodiment of the invention and are not intended to limit the invention thereto.

FIG. 1 is a block diagram of one embodiment of a stress reduction and sleep promotion system. The stress reduction and sleep promotion system 700 includes body sensors 702, environmental sensors 704, a remote device 511 with local storage 706, a remote server 708, and system components 710. The body sensors 702 include a posture sensor 711, a respiration sensor 712, an electrooculography (EOG) sensor 713, a heart rate sensor 714, a body weight sensor 715, a movement sensor 716, an electromyography (EMG) sensor 717, a brain wave sensor 718, a body temperature sensor 720, an analyte sensor 721, a pulse oximeter sensor 722, a blood pressure (BP) sensor 723, an electrodermal activity (EDA) sensor 724, and/or a body fat sensor 725. In one embodiment, at least one body sensor 702 is implanted in the body of a user. In a preferred embodiment, at least one body sensor 702 is operable to transmit data to the remote device 511 and/or the remote server 708 in real time.

The posture sensor 711 measures a posture of an individual. In one embodiment, the posture sensor 711 includes at least one pressure sensor. The at least one pressure sensor is preferably embedded in a seat and/or seat cushion (e.g., DARMA, SENSIMAT). In another embodiment, the posture sensor 711 is a wearable device (e.g., LUMOBACK Posture Sensor). In another embodiment, the posture sensor 711 includes at least one camera. The at least one camera is operable to detect a posture of the individual using, e.g., computer vision.

The respiration sensor 712 measures a respiratory rate. In one embodiment, the respiration sensor 712 is incorporated into a wearable device (e.g., a chest strap). In another embodiment, the respiration sensor 712 is incorporated into a patch or a bandage. Alternatively, the respiratory rate is estimated from an electrocardiogram, a photoplethysmogram (e.g., a pulse oximeter), and/or an accelerometer. In yet another embodiment, the respiratory sensor 712 uses a non-contact motion sensor to monitor respiration.

The electrooculography (EOG) sensor 713 measures the corneo-retinal standing potential that exists between the front and the back of the eye. Measurements of eye movements are done by placing pairs of electrodes either above and below the eye or to the left and right of the eye. If the eye moves to a position away from the center and toward one of the electrodes, a potential difference occurs between the electrodes. The recorded potential is a measure of the eye's position.

The heart sensor 714 is preferably incorporated into a wearable device (e.g., APPLE WATCH, FITBIT, SAMSUNG GALAXY WATCH). Alternatively, the heart sensor 714 is attached to the user with a chest strap. In another embodiment, the heart sensor 714 is incorporated into a patch or a bandage. In still another embodiment, the heart sensor 714 is a ring (e.g., OURA). In yet another embodiment, the heart sensor 714 is incorporated into a sensor device on or under the mattress (e.g., BEDDIT, EMFIT QS). A heart rate is determined using electrocardiography, pulse oximetry, ballistocardiography, or seismocardiography. In one embodiment, the heart sensor 714 measures heart rate variability (HRV). HRV is a measurement of the variation in time intervals between heartbeats. A high HRV measurement is indicative of less stress, while a low HRV measurement is indicative of more stress. Studies have linked abnormalities in HRV to diseases where stress is a factor (e.g., diabetes, depression, congestive heart failure). In one embodiment, a Poincaré plot is generated to display HRV on a device such as a smartphone. In another embodiment, the heart sensor 714 is an electrocardiogram.

The body weight sensor 715 is preferably a smart scale (e.g., FITBIT ARIA, WITHINGS BODY+, GARMIN INDEX,). Alternatively, the body weight sensor 715 is at least one pressure sensor embedded in a mattress or a mattress topper. In one embodiment, the stress reduction and sleep promotion system 700 is also operable to determine a height of a user using the at least one pressure sensor embedded in a mattress or a mattress topper. In another embodiment, a body mass index (BMI) of the user is calculated using the body weight of the user and the height of the user as measured by the at least one pressure sensor.

The movement sensor 716 is an accelerometer and/or a gyroscope. In one embodiment, the accelerometer and/or the gyroscope are incorporated into a wearable device (e.g., FITBIT, APPLE WATCH, SAMSUNG GALAXY WATCH, actigraph). In another embodiment, the accelerometer and/or the gyroscope are incorporated into a smartphone. In alternative embodiment, the movement sensor 716 is a non-contact sensor. In one embodiment, the movement sensor 716 is at least one piezoelectric sensor. In another embodiment, the movement sensor 716 is a pyroelectric infrared sensor (i.e., a "passive" infrared sensor). In yet another embodiment, the movement sensor 716 is at least one pressure sensor embedded in a mattress or mattress topper. Alternatively, the movement sensor 716 is incorporated into a smart fabric. In still another embodiment, the movement sensor 716 is operable to analyze a gait of a user.

The electromyography (EMG) sensor 717 records the electrical activity produced by skeletal muscles. Impulses are recorded by attaching electrodes to the skin surface over the muscle. In a preferred embodiment, three electrodes are placed on the chin. One in the front and center and the other two underneath and on the jawbone. These electrodes demonstrate muscle movement during sleep, which can be used to detect REM or NREM sleep. In another embodiment, two electrodes are placed on the inside of each calf muscle about 2 to 4 cm (about 0.8 to 1.6 inches) apart. In yet another embodiment, two electrodes are placed over the anterior tibialis of each leg. The electrodes on the leg can be used to detect movement of the legs during sleep, which may occur with Restless Leg Syndrome or Periodic Limb Movements of Sleep.

The brain wave sensor 718 is preferably an electroencephalogram (EEG) with at least one channel. In a preferred embodiment, the EEG has at least two channels. Multiple channels provide higher resolution data. The frequencies in EEG data indicate particular brain states. The brain wave sensor 718 is preferably operable to detect delta, theta, alpha, beta, and gamma frequencies. In another embodiment, the brain wave sensor 718 is operable to identify cognitive and emotion metrics, including focus, stress, excitement, relaxation, interest, and/or engagement. In yet another embodiment, the brain wave sensor 718 is operable to identify cognitive states that reflect the overall level of engagement, attention and focus and/or workload that reflects cognitive processes (e.g., working memory, problem solving, analytical reasoning).

The energy field sensor 719 measures an energy field of a user. In one embodiment, the energy field sensor 719 is a gas discharge visualization (GDV) device. Examples of a GDV device are disclosed in U.S. Pat. Nos. 7,869,636 and 8,321,010 and U.S. Publication No. 20100106424, each of which is incorporated herein by reference in its entirety. The GDV device utilizes the Kirlian effect to evaluate an energy field. In a preferred embodiment, the GDV device utilizes a high-intensity electric field (e.g., 1024 Hz, 10 kV, square pulses) input to an object (e.g., human fingertips) on an electrified glass plate. The high-intensity electric field produces a visible gas discharge glow around the object (e.g., fingertip). The visible gas discharge glow is detected by a charge-coupled detector and analyzed by software on a computer. The software characterizes the pattern of light emitted (e.g., brightness, total area, fractality, density). In a preferred embodiment, the software utilizes Mandel's Energy Emission Analysis and the Su-Jok system of acupuncture to create images and representations of body systems. The energy field sensor 719 is preferably operable to measure stress levels, energy levels, and/or a balance between the left and right sides of the body.

The body temperature sensor 720 measures core body temperature and/or skin temperature. The body temperature sensor 720 is a thermistor, an infrared sensor, or thermal flux sensor. In one embodiment, the body temperature sensor 720 is incorporated into an armband or a wristband. In another embodiment, the body temperature sensor 720 is incorporated into a patch or a bandage. In still another embodiment, the body temperature sensor 720 is incorporated into a ring (e.g., OURA). In yet another embodiment, the body temperature sensor 720 is an ingestible core body temperature sensor (e.g., CORTEMP). The body temperature sensor 720 is preferably wireless.

The analyte sensor 721 monitors levels of an analyte in blood, sweat, or interstitial fluid. In one embodiment, the analyte is an electrolyte, a small molecule (molecular weight<900 Daltons), a protein (e.g., C-reactive protein), and/or a metabolite. In another embodiment, the analyte is glucose, lactate, glutamate, oxygen, sodium, chloride, potassium, calcium, ammonium, copper, magnesium, iron, zinc, creatinine, uric acid, oxalic acid, urea, ethanol, an amino acid, a hormone (e.g., cortisol, melatonin), a steroid, a neurotransmitter, a catecholamine, a cytokine, and/or an interleukin (e.g., IL-6). The analyte sensor 721 is preferably non-invasive. Alternatively, the analyte sensor 721 is minimally invasive or implanted. In one embodiment, the analyte sensor 721 is incorporated into a wearable device. Alternatively, the analyte sensor 721 is incorporated into a patch or a bandage.

The pulse oximeter sensor 722 monitors oxygen saturation. In one embodiment, the pulse oximeter sensor 722 is worn on a finger, a toe, or an ear. In another embodiment, the pulse oximeter sensor 722 is incorporated into a patch or a bandage. The pulse oximeter sensor 722 is preferably wireless. Alternatively, the pulse oximeter sensor 722 is wired. In one embodiment, the pulse oximeter sensor 722 is connected by a wire to a wrist strap or a strap around a hand. In another embodiment, the pulse oximeter sensor 722 is combined with a heart rate sensor 714. In yet another embodiment, the pulse oximeter sensor 722 uses a camera lens on a smartphone or a tablet.

The blood pressure (BP) sensor 723 is a sphygmomanometer. The sphygmomanometer is preferably wireless. Alternatively, the blood pressure sensor 723 estimates the blood pressure without an inflatable cuff (e.g., SALU PULSE+). In one embodiment, the blood pressure sensor 723 is incorporated into a wearable device.

The electrodermal activity sensor 724 measures sympathetic nervous system activity. Electrodermal activity is more likely to have high frequency peak patterns (i.e., "storms") during deep sleep. In one embodiment, the electrodermal activity sensor 724 is incorporated into a wearable device. Alternatively, the electrodermal activity sensor 724 is incorporated into a patch or a bandage.

The body fat sensor 725 is preferably a bioelectrical impedance device. In one embodiment, the body fat sensor 725 is incorporated into a smart scale (e.g., FITBIT ARIA, WITHINGS BODY+, GARMIN INDEX). Alternatively, the body fat sensor 725 is a handheld device.

The environmental sensors 704 include an environmental temperature sensor 726, a humidity sensor 727, a noise sensor 728, an air quality sensor 730, a light sensor 732, a motion sensor 733, and/or a barometric sensor 734. In one embodiment, the environmental temperature sensor 726, the humidity sensor 727, the noise sensor 728, the air quality sensor 730, the light sensor 732, the motion sensor 733, and/or the barometric sensor 734 are incorporated into a home automation system (e.g., AMAZON ALEXA, APPLE HOMEKIT, GOOGLE HOME, IF THIS THEN THAT (IF-TTT)). Alternatively, the environmental temperature sensor 726, the humidity sensor 727, the noise sensor 728, and/or the light sensor 732 are incorporated into a smartphone or tablet. In one embodiment, the noise sensor 728 is a microphone. In one embodiment, the air quality sensor 730 measures carbon monoxide, carbon dioxide, nitrogen dioxide, sulfur dioxide, particulates, and/or volatile organic compounds (VOCs). In another embodiment, at least one environmental sensor 704 is operable to transmit data to the remote device 511 and/or the remote server 708 in real time.

The remote device 511 is preferably a smartphone or a tablet. Alternatively, the remote device 511 is a laptop or a desktop computer. The remote device 511 includes a processor 760, an analytics engine 762, a control interface 764, and a user interface 766. The remote device 511 accepts data input from the body sensors 702 and/or the environmental sensors 704. The remote device also accepts data input from the remote server 708. The remote device 511 stores data in a local storage 706.

The local storage 706 on the remote device 511 includes a user profile 736, historical subjective data 738, predefined programs 740, custom programs 741, historical objective data 742, and historical environmental data 744. The user profile 736 stores stress reduction and sleep promotion system preferences and information about the user, including but not limited to, age, weight, height, gender, medical history (e.g., sleep conditions, medications, diseases), fitness (e.g., fitness level, fitness activities), sleep goals, stress level, and/or occupational information (e.g., occupation, shift information). The medical history includes caffeine consumption, alcohol consumption, tobacco consumption, use of prescription sleep aids and/or other medications, use of nutritional supplements, blood pressure, restless leg syndrome, narcolepsy, headaches, heart disease, sleep apnea, depression, stroke, diabetes, insomnia, anxiety or posttraumatic stress disorder (PTSD), and/or neurological disorders.

In one embodiment, the medical history incorporates information gathered from the Epworth Sleepiness Scale (ESS), the Insomnia Severity Index (ISI), Generalized Anxiety Disorder 7-item (GAD-7) Scale, and/or Patient Heath Questionanaire-9 (PHQ-9) (assessment of depression). The ESS is described in Johns M W (1991). "A new method for measuring daytime sleepiness: the Epworth sleepiness scale", *Sleep,* 14 (6): 540-5, which is incorporated herein by reference in its entirety. The ISI is described in Morin et al. (2011). "The Insomnia Severity Index: Psychometric Indicators to Detect Insomnia Cases and Evaluate Treatment Response", *Sleep,* 34(5): 601-608, which is incorporated herein by reference in its entirety. The GAD-7 is described in Spitzer et al., "A brief measure for assessing generalized anxiety disorder: the GAD-7 ", *Arch Intern Med.,* 2006 May 22; 166(1):1092-7, which is incorporated herein by reference in its entirety. The PHQ-9 is described in Kroenke et al., "The PHQ-9: Validity of a Brief Depression Severity Measure", *J. Gen. Intern. Med.,* 2001 September; 16(9): 606-613, which is incorporated herein by reference in its entirety.

In one embodiment, the weight of the user is automatically uploaded to the local storage from a third-party application. In one embodiment, the third-party application obtains the information from a smart scale (e.g., FITBIT ARIA, NOKIA BODY+, GARMIN INDEX). In another embodiment, the medical history includes information gathered from a Resting Breath Hold test.

The historical objective data 742 includes information gathered from the body sensors 702. This includes information from the respiration sensor 712, the electrooculography sensor 713, the heart sensor 714, the movement sensor 716, the electromyography sensor 717, the brain wave sensor 718, the energy field sensor 719, the body temperature sensor 720, the analyte sensor 721, the pulse oximeter sensor 722, the blood pressure sensor 723, and/or the electrodermal activity sensor 724. In another embodiment, the historical objective data 742 includes information gathered from the Maintenance of Wakefulness Test, the Digit Symbol Substitution Test, and/or the Psychomotor Vigilance Test. The Maintenance of Wakefulness Test is described in Doghramji, et al., "A normative study of the maintenance of wakefulness test (MWT)", *Electroencephalogr. Clin. Neurophysiol.*, 1997 November; 103(5): 554-562, which is incorporated herein by reference in its entirety. The Digit Symbol Substitution Test is described in Wechsler, D. (1997). Wechsler Adult Intelligence Scale—Third edition (WAIS-III). San Antonio, Tex.: Psychological Corporation and Wechsler, D. (1997). Wechsler Memory Scale—Third edition (WMS-III). San Antonio, Tex.: Psychological Corporation, each of which is incorporated herein by reference in its entirety. The Psychomotor Vigilance Test is described in Basner et al., "Maximizing sensitivity of the psychomotor vigilance test (PVT) to sleep loss", *Sleep*, 2011 May 1; 34(5): 581-91, which is incorporated herein by reference in its entirety.

The historical environmental data 744 includes information gathered from the environmental sensors 704. This includes information from the environmental temperature sensor 726, the humidity sensor 727, the noise sensor 728, the air quality sensor 730, the light sensor 732, and/or the barometric sensor 734.

The historical subjective data 738 includes information regarding sleep and/or stress. In one embodiment, the information regarding sleep is gathered from manual sleep logs (e.g., Pittsburgh Sleep Quality Index). The manual sleep logs include, but are not limited to, a time sleep is first attempted, a time to fall asleep, a time of waking up, hours of sleep, number of awakenings, times of awakenings, length of awakenings, perceived sleep quality, use of medications or supplements to assist with sleep, difficulty staying awake and/or concentrating during the day, difficulty with temperature regulation at night (e.g., too hot, too cold), trouble breathing at night (e.g., coughing, snoring), having bad dreams, waking up in the middle of the night or before a desired wake up time, twitching or jerking in the legs while asleep, restlessness while asleep, difficulty sleeping due to pain, and/or needing to use the bathroom in the middle of the night. The Pittsburgh Sleep Quality Index is described in Buysse, et al., "The Pittsburgh sleep quality index: A new instrument for psychiatric practice and research". *Psychiatry Research*. 28 (2): 193-213 (May 1989), which is incorporated herein by reference in its entirety.

In another embodiment, the historical subjective data 738 includes information gathered regarding sleepiness (e.g., Karolinska Sleepiness Scale, Stanford Sleepiness Scale, Epworth Sleepiness Scale). The Karolinska Sleepiness Scale is described in Åkerstedt, et al., "Subjective and objective sleepiness in the active individual", *Int J Neurosc.*, 1990; 52:29-37 and Baulk et al., "Driver sleepiness—evaluation of reaction time measurement as a secondary task", *Sleep*, 2001; 24(6):695-698, each of which is incorporated herein by reference in its entirety. The Stanford Sleepiness Scale is described in Hoddes E. (1972). "The development and use of the Stanford sleepiness scale (SSS)". *Psychophysiology*. 9 (150) and Maclean, et al. (1992-03-01). "Psychometric evaluation of the Stanford Sleepiness Scale". *Journal of Sleep Research*. 1 (1): 35-39, each of which is incorporated herein by reference in its entirety.

In yet another embodiment, the historical subjective data 738 includes information regarding tension or anxiety, depression or dejection, anger or hostility, and/or fatigue or inertia gathered from the Profile of Mood States. The Profile of Mood States is described in the Profile of Mood States, $2^{nd}$ Edition published by Multi-Health Systems (2012) and Curran et al., "Short Form of the Profile of Mood States (POMS-SF): Psychometric information", *Psychological Assessment*. 7 (1): 80-83 (1995), each of which is incorporated herein by reference in its entirety. In another embodiment, the historical subjective data 738 includes information gathered from the Ford Insomnia Response to Stress Test (FIRST), which asks how likely a respondent is to have difficulty sleeping in nine different situations. The FIRST is described in Drake et al., "Vulnerability to stress-related sleep disturbance and hyperarousal", *Sleep*, 2004; 27:285-91 and Drake et al., "Stress-related sleep disturbance and polysomnographic response to caffeine", *Sleep Med.*, 2006; 7:567-72, each of which is incorporated herein by reference in its entirety. In still another embodiment, the historical subjective data 738 includes information gathered from the Impact of Events, which assesses the psychological impact of stressful life events. A subscale score is calculated for intrusion, avoidance, and/or hyperarousal. The Impact of Events is described in Weiss, D. S., & Marmar, C. R. (1996). The Impact of Event Scale—Revised. In J. Wilson & T. M. Keane (Eds.), Assessing psychological trauma and PTSD (pp. 399-411). New York: Guilford, which is incorporated herein by reference in its entirety. In one embodiment, the historical subjective data 738 includes information gathered from the Social Readjustment Rating Scale (SRRS). The SRRS lists 52 stressful life events and assigns a point value based on how traumatic the event was determined to be by a sample population. The SRRS is described in Holmes et al., "The Social Readjustment Rating Scale", *J. Psychosom. Res.* 11(2): 213-8 (1967), which is incorporated herein by reference in its entirety.

In one embodiment, the predefined programs 740 are general sleep settings for various conditions and/or body types (e.g., weight loss, comfort, athletic recovery, hot flashes, bed sores, depression, multiple sclerosis, alternative sleep cycles). In one embodiment, a weight loss predefined program sets a surface temperature at a very cold setting (e.g., 15.56-18.89° C. (60-66° F.)) to increase a metabolic response, resulting in an increase in calories burned, which then leads to weight loss. Temperature settings are automatically adjusted to be as cold as tolerable by the user after the first sleep cycle starts to maximize the caloric burn while having the smallest impact on sleep quality. The core temperature of an overweight individual may fail to drop due to a low metabolism. In one example, the surface temperature is 20° C. (68° F.) at the start of a sleep period, 18.89° C. (66° F.) during N1-N2 sleep, 18.33° C. (65° F.) during N3 sleep, 19.44° C. (67° F.) during REM sleep, and 20° C. (68° F.) to wake the user.

In one embodiment, the custom programs 741 are sleep settings defined by the user. In one example, the user creates a custom program by modifying a predefined program (e.g., the weight loss program above) to be 1.11° C. (2° F.) cooler during the N3 stage. In another example, the user creates a custom program by modifying a predefined program to have a start temperature of 37.78° C. (100° F.). The custom programs 741 allow a user to save preferred sleep settings.

The remote server 708 includes global historical subjective data 746, global historical objective data 748, global historical environmental data 750, global profile data 752, a global analytics engine 754, a calibration engine 756, a simulation engine 758, and a reasoning engine 759. The global historical subjective data 746, the global historical objective data 748, the global historical environmental data 750, and the global profile data 752 include data from multiple users.

The system components 710 include a mattress pad 11 with adjustable temperature control or other temperature regulating article (e.g., blanket, mattress, chair pad), a mattress with adjustable firmness 768, a mattress with adjustable elevation 770, an alarm clock 772, a thermostat to adjust the room temperature 774, a lighting system 776, a fan 778, a humidifier 780, a dehumidifier 782, a pulsed electromagnetic field (PEMF) device 784, a transcutaneous electrical nerve stimulation (TENS) device 785, a sound generator 786, an air purifier 788, a scent generator 790, a red light and/or near-infrared lighting device 792, a sunrise simulator 793, and/or a sunset simulator 794.

The body sensors 702, the environmental sensors 704, the remote device 511 with local storage 706, the remote server 708, and the system components 710 are designed to connect directly (e.g., Universal Serial Bus (USB) or equivalent) or wirelessly (e.g., BLUETOOTH, WI-FI, ZIGBEE) through systems designed to exchange data between various data collection sources. In a preferred embodiment, the body sensors 702, the environmental sensors 704, the remote device 511 with local storage 706, the remote server 708, and the system components 710 communicate wirelessly through BLUETOOTH. Advantageously, BLUETOOTH emits lower electromagnetic fields (EMFs) than WI-FI and cellular signals.

Additional information regarding the stress reduction and sleep promotion system is in U.S. Publication Nos. 20180000255 and 20180110960 and U.S. application Ser. No. 16/686,394 filed Nov. 18, 2019, each of which is incorporated herein by reference in its entirety. Additional information regarding sleep recovery is in U.S. application Ser. No. 16/715,652 filed Dec. 16, 2019, which is incorporated herein by reference in its entirety.

Figure 2:
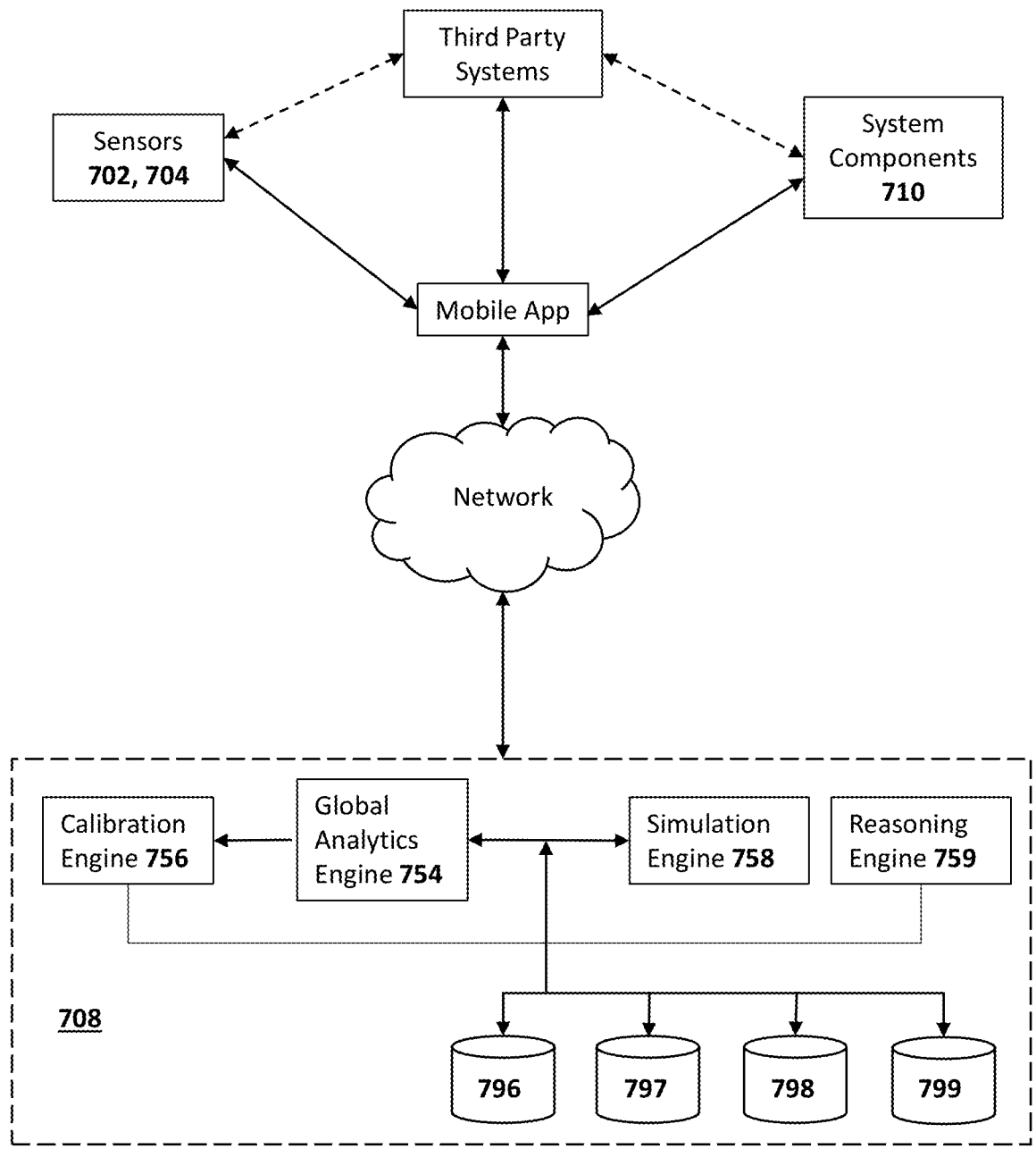
FIG. 2 is a block diagram of one embodiment of the system architecture of the stress reduction and sleep promotion system.

As shown in FIG. 2, in one embodiment, the remote server 708 hosts a global analytics engine 754, a calibration engine 756, a simulation engine 758, a reasoning engine 759, and databases 796, 797, 798, and 799. Although four databases are shown, it is equally possible to have any number of databases greater than one. The global analytics engine 754 generates predicted values for a monitored stress reduction and sleep promotion system using a virtual model of the stress reduction and sleep promotion system based on real-time data. The calibration engine 756 modifies and updates the virtual model based on the real-time data. Any operational parameter of the virtual model may be modified by the calibration engine 756 as long as the resulting modification is operable to be processed by the virtual model.

The global analytics engine 754 analyzes differences between the predicted values and optimized values. If the difference between the optimized values and the predicted values is greater than a threshold, then the simulation engine 758 determines optimized values of the monitored stress reduction and sleep promotion system based on the real-time data and user preferences. In one embodiment, the global analytics engine 754 determines whether a change in parameters of the system components 710 is necessary to optimize sleep based on the output of the simulation engine 758. If a change in parameters is necessary, the new parameters are transmitted to a mobile application on the remote device and then to the system components 710. The calibration engine 756 then updates the virtual model with the new parameters. Thus, the system autonomously optimizes the stress reduction and sleep promotion system (e.g., surface temperature) without requiring input from a user.

In another embodiment, the remote server 708 includes a reasoning engine 759 built with artificial intelligence (AI) algorithms. The reasoning engine 759 is operable to generate a reasoning model based on multiple sets of training data. The multiple sets of training data are a subset of global historical subjective data, global historical objective data, global historical environmental data, and global profile data. For example, a user's stress level and/or sleep efficiency significantly improve after engaging in an activity over a period of time, which is then included in the training data. The training data includes context data (e.g., baseline data, body sensor data) and action data (e.g., activity data, system component use). The reasoning model is updated periodically when there is an anomaly indicated in the action data produced by the reasoning data based on the context data. Each of U.S. Pat. No. 9,922,286 titled "Detecting and Correcting Anomalies in Computer-Based Reasoning Systems" and U.S. application Ser. No. 15/900,398 is incorporated herein by reference in its entirety.

Figure 3:
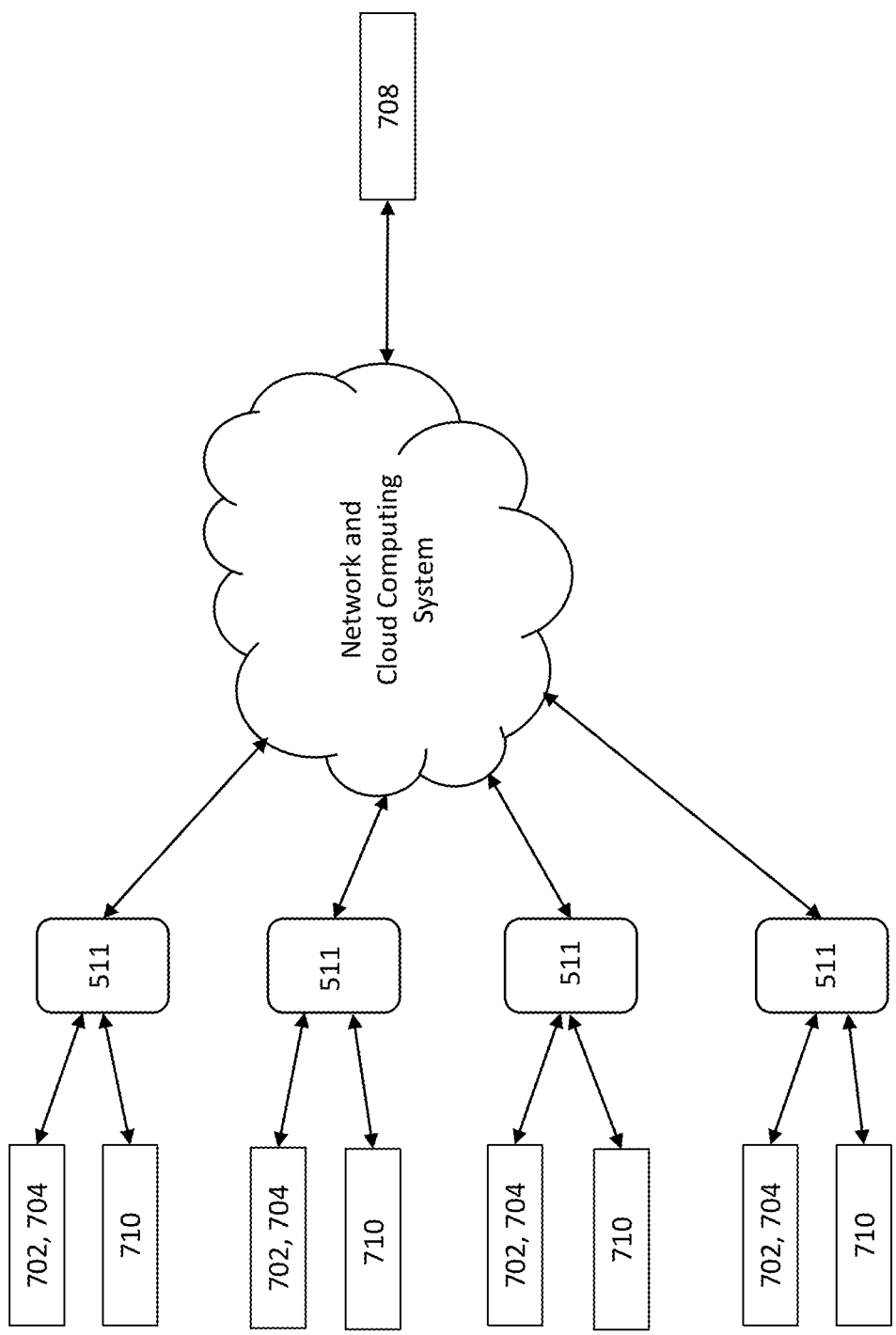
FIG. 3 is an illustration of a network of stress reduction and sleep promotion systems.

FIG. 3 is an illustration of a network of stress reduction and sleep promotion systems. Data from multiple users are operable to be stored on a remote server 708. The remote server 708 is connected through a network and cloud computing system to a plurality of remote devices 511. Each of the plurality of remote devices 511 is connected to body sensors 702 and/or environmental sensors 704, as well as system components 710. Although one remote server is shown, it is equally possible to have any number of remote servers greater than one. A user may opt into sending their data to the remote server 708, which is stored in at least one database on the remote server 708. The simulation engine on the remote server 708 is operable to use data from the multiple users to determine customized and optimized sleep settings for the user based on personal preferences (e.g., a target number of hours of sleep, a preferred bed time, a preferred wake time, a faster time to fall asleep, fewer awakenings during the sleeping period, more REM sleep, more deep sleep, and/or a higher sleep efficiency) or physical condition (e.g., weight loss, comfort, athletic recovery, hot flashes, bed sores, depression). In one example, the temperature settings for a temperature-conditioned mattress pad for a user with hot flashes are automatically determined by the simulation engine examining data obtained from other users with hot flashes and a temperature-conditioned mattress pad stored in databases on the remote server. The simulation engine is also operable to use data from the multiple users to provide recommendations (e.g., activities, system components) to users with a similar background (e.g., gender, age, health condition).

The stress reduction and sleep promotion system includes a virtual model of the stress reduction and sleep promotion system. The virtual model is initialized based on the program selected. The virtual model of the stress reduction and sleep promotion system is dynamic, changing to reflect the status of the stress reduction and sleep promotion system in real time or near real time. The virtual model includes information from the body sensors and the environmental sensors. Based on the data from the body sensors and the environmental sensors, the virtual model generates predicted values for the stress reduction and sleep promotion system. A sleep stage (e.g., awake, Stage N1, Stage N2, Stage N3, REM sleep) for the user is determined from the data from the body sensors.

The stress reduction and sleep promotion system is monitored to determine if there is a change in status of the body sensors (e.g., change in body temperature), the environmental sensors (e.g., change in room temperature), the system components (e.g., change in temperature of mattress pad), or sleep stage of the user. If there is a change in status, the virtual model is updated to reflect the change in status. Predicted values are generated for the stress reduction and sleep promotion system. If a difference between the optimized values and the predicted values is greater than a threshold, a simulation is run on the simulation engine to optimize the stress reduction and sleep promotion system based on the real-time data. The simulation engine uses information including, but not limited to, global historical subjective data, global historical objective data, global historical environmental data, and/or global profile data to determine if a change in parameters is necessary to optimize the stress reduction and sleep promotion system. In one example, the temperature of the mattress pad is lowered to keep a user in Stage N3 sleep for a longer period of time. In another example, the mobile application provides recommendations of an activity to a user.

As previously mentioned, the at least one remote device preferably has a user interface (e.g., a mobile application for a smartphone or tablet) that allows the stress reduction and sleep promotion system to adjust the parameters of the stress reduction and sleep promotion system. The parameters of the stress reduction and sleep promotion system (e.g., target temperatures of a mattress pad) are operable to be manipulated through the sleeping period using a predefined program or a customized program based on user preferences to produce a deeper, more restful sleep.

Because the target temperatures may be set at any time, those target temperatures may be manipulated through the sleeping period in order to match user preferences or a program to correlate with user sleep cycles to produce a deeper, more restful sleep.

In one embodiment, the mobile application measures a time when a user began attempting to sleep (TATS), a TATS start time, a TATS end time, a time in bed (TIB), a TIB start time, and/or a TIB end time. The mobile application calculates a total TATS duration based on the TATS start time and the TATS end time. The mobile application also calculates a total TIB duration based on the TIB start time and the TIB end time. In one embodiment, the TATS start time, the TATS end time, the TIB start time, and/or the TIB end time are indicated by the user (e.g., by pressing a button in the mobile application). Alternatively, the TATS start time, the TATS end time, the TIB start time, and/or the TIB end time are determined by sensors. In one example, the TATS start time is determined by a user's eyes closing while in bed. In another example, the TATS end time is determined by increased motion as measured by a movement sensor and/or opening of the eyes. In yet another example, the TIB start time is determined by sensors indicating a user is horizontal and/or bed or room sensors indicating the user is in bed. In still another example, the TIB end time is determined by sensors indicating a user is not horizontal and/or bed or room sensors indicating the user is not in bed.

The mobile application is operable to determine whether a user is awake or asleep. The state of wakefulness (i.e., "awake") is characterized by cognitive awareness and/or consciousness, responsiveness to environmental cues, sustained movement detected by a movement sensor, beta and/or alpha waves as detected by EEG, increased heart rate, increased respiration, increased blood pressure, increased electrodermal activity, increased body temperature, open eyes, voluntary eye movements, and/or increased EMG on the chin. The state of sleep (i.e., "asleep") is characterized by loss of alertness and/or consciousness, lack of response to environmental cues, lack of movement, reduction in alpha waves as detected by EEG, increased theta and delta waves as detected by EEG, decreased heart rate, decreased respiration, decreased blood pressure, decreased body temperature, closed eyes, eye twitches, and/or decreased oxygen saturation.

In a preferred embodiment, the mobile application is operable to measure an initial sleep onset time and/or a final awakening time. The initial sleep onset time is a first occurrence of sleep after the TATS start time. The final awakening time is a time immediately after the last occurrence of sleep before the TATS end time. In one embodiment, the mobile application calculates a latency to sleep onset as the duration of a time interval between the TATS start time to the initial sleep onset time. In another embodiment, the mobile application calculates a latency to arising as the duration of a time interval between the final awakening time to the TATS end time. In a preferred embodiment, the mobile application is operable to calculate a sleep efficiency percentage. In one embodiment, the sleep efficiency percentage is defined as the total sleep time divided by the total TATS duration. In an alternative embodiment, the sleep efficiency percentage is defined as the total sleep time divided by the total TIB duration.

In one embodiment, the mobile application is operable to determine a total sleep period duration, a total sleep time, a sleep maintenance percentage, a total wakefulness duration, a wakefulness duration after initial sleep onset, a total number of awakenings, an awakening rate per hour, and/or a sleep fragmentation rate.

In another embodiment, the mobile application is operable to determine REM sleep, N1 sleep, N2 sleep, and/or N3 sleep. REM sleep is characterized by low-voltage, mixed-frequency EEG activity with less than 15 seconds of alpha activity, saw-tooth theta EEG activity, rapid eye movements, and/or decreased or absent EMG activity on the chin. N1 sleep is characterized by low-voltage, mixed-frequency EEG activity with less than 15 seconds of alpha activity in a 30-second epoch, no sleep spindles or K complexes, possible slow rolling eye movements, and/or diminished EMG activity on the chin. N2 sleep is characterized by sleep spindle and/or K complex activity, absence of eye movements, and/or diminished EMG activity on the chin. N3 sleep is characterized by high amplitude (e.g., greater than 75 µV peak-to-peak), slow wave (e.g., frequency of 4 Hz or less) EEG activity. In yet another embodiment, the mobile application is operable to calculate REM sleep duration, percentage, and latency from sleep onset; N1 sleep duration, percentage, and latency from sleep onset; N2 sleep duration, percentage, and latency from sleep onset; and/or N3 sleep duration, percentage, and latency from sleep onset.

Alternatively, the calculations and determining of sleep states described above are determined over the network on a remote server. In one embodiment, the calculations and determining of sleep states are then transmitted to at least one remote device. In yet another embodiment, the calculations and determining of sleep states described above are determined using third party software and transmitted to the mobile application.

The mobile application preferably serves as a hub to interface with the system components, the body sensors, the environmental sensors, and/or at least one third-party application (e.g., APPLE HEALTH, MYFITNESSPAL, nutrition tracker). The mobile application is operable to obtain data from a mattress pad or other temperature-regulating article (e.g., OOLER, CHILIBLANKET, temperature-regulated mattress) and/or a wearable (e.g., OURA, APPLE WATCH, FITBIT). The mobile application is operable to recognize patterns the user does not already see and help guide them to a new pattern. For example, many nutrition trackers monitor food and water intake and set daily and long-term calorie and weight goals. However, these nutrition trackers do not combine this information with additional data. In one example, data from the nutrition tracker is combined with GPS information to prompt a user before they eat fast food. The mobile application uses the chatbot to interact with the user before they eat fast food (e.g., positive quote, breathing exercise, reminder about goals). Additionally, the mobile application encourages the user to add the food into the mobile application and/or third-party application before they eat so the user is aware of what they are consuming. The mobile application also is operable to propose a meal for the user and/or an exercise plan that allows the user to meet goals or minimize damage from the fast food.

Additionally, the mobile application uses cognitive behavioral therapy (CBT) with artificial intelligence (AI) to help a user make incremental changes to improve sleep and health. CBT relies on three components: actions, thoughts, and feelings. The mobile application encourages activities, positive thoughts, and social interaction to increase happiness and decrease depression. The mobile application preferably uses a chatbot to interact with the user. Alternatively, the mobile application has at least one coach to interact with the user. The mobile application is operable to provide repetitive coaching, which is necessary for long-term habit change. For example, the mobile application reminds a user to take a vitamin every morning until the user begins logging the action on their own. The mobile application also reminds the user to take the vitamin when the user does not log the action. The mobile application is also operable to assist a user in creating positive coping mechanisms to manage and diffuse stress daily. For example, the mobile application learns over time that the user enjoys walking for stress relief. When the mobile application detects that a user is stressed, the mobile application recommends taking a walk. Further, the mobile application is operable to understand natural language voices, converse with the user, and execute voice commands.

The mobile application uses machine learning to identify positive behaviors, negative behaviors, antecedents or causes of positive behaviors, antecedents or causes of negative behaviors, triggers, early or past experiences that impact current behavior, and/or core belief structures and patterns. The mobile application is also operable to use machine learning to identify timing of the positive behaviors, the negative behaviors, the antecedents or causes of positive behaviors, the antecedents or causes of negative behaviors, and/or the triggers. The timing is a daily, weekly, monthly, or other interval (e.g., two weeks, six weeks) basis.

The mobile application also uses machine learning to identify patterns of habits and behaviors. For example, the mobile application is operable to determine when to push notifications based on when a user is likely to be looking at their phone (e.g., before work, during lunch, after work). The mobile application is also operable to determine when a user is stressed (e.g., via user identification and/or sensor data). In one embodiment, the machine learning incorporates information, including, but not limited to, mobile phone usage, mobile application usage, GPS location, and/or sensor data.

In one embodiment, the mobile application asks the user to identify at least one problem the user wants to improve. The mobile application is operable to identify patterns, triggers, and stimuli for stress. In another embodiment, the mobile application is operable to analyze the at least one problem to determine which one of the at least one problem is easiest for the user to remedy. In one example, the mobile application prioritizes the one of the at least one problem. Advantageously, this allows the user to experience success with achieving a goal, providing motivation to tackle additional problems. The mobile application is operable to document a user's progress over time. In one embodiment, the mobile application provides positive feedback to a user when goals are achieved. In another embodiment, the mobile application is operable to designate at least one goal based on an amount of time to achieve the at least one goal (e.g., short term goal, medium term goal, long term goal).

In another embodiment, the mobile application provides a journaling component. In one example, a user is worried about financial problems, which are addressable via budget, planning, and/or organization tips via the mobile application. However, the journaling component provides a way to document and validate the user's stress, allowing the user to focus on other tasks during the day and sleep at night. In one embodiment, the journaling component includes a gratitude journal.

The mobile application preferably provides a social network component for a user to interact with other users with similar interests or health conditions. In one embodiment, the mobile application identifies at least one group for a user based on health markers, mental health markers, goals, age, gender, social and economic groups, religion, etc. The social network component also allows for the creation of sharing groups that promote trust. In one example, the mobile application allows for the creating of a sharing group dedicated to domestic abuse survivors to provide emotional support to members of the group. Further, patterns of response trigger movement between groups. For example, a user with social anxiety falls into multiple groups, but based on their response to interventions and the types of interventions that are having success, the prediction of what will help the most and, therefore, the group assignment will change. In another example, an overweight user with sleep apnea who loses weight and remedies the sleep apnea naturally will move out of the sleep apnea group after the weight loss. However, that user may also move into a group that focuses on social anxiety and/or using food as a coping mechanism. Additionally, the social network component allows for a user to challenge other users to complete activities.

The mobile application allows a user to identify stress, label the source of the stress, and put users into patterns of emotions, thoughts, and behaviors to categorize intervention suggestions. In one example, a user suffers from social anxiety and, therefore, avoids phone calls and large group events. The mobile application allows a user to rank activities based on stress level (e.g., scale from 1 to 10). The mobile application provides suggestions for how to manage stress and requests feedback from the user to identify what is working. For example, the mobile application encourages a user to meditate both before and after a large group event. Additionally, the mobile application provides a checklist and measurements for success.

In another example, the mobile application assists a user through a death. Based on time and patterns for grief (e.g., Kübler-Ross model), the mobile application encourages a user through the process of healing. The mobile application includes visualization exercises (e.g., visualizing putting bigger hurts in a closet and taking them out in small moments). The mobile application is operable to map a tree of support (e.g., family, friends, other users of the mobile application). The mobile application provides a positive quote, encourages meditation, and/or encourages a walk when the user is having a bad day (e.g., as noted by the user and/or detected by sensors).

In a preferred embodiment, the mobile application includes geolocation data. The geolocation data allows for targeted suggestions that are relevant to a user's location. For example, the mobile application suggests activities (e.g., races, events) located near the user. Additionally, geolocation data allows for tracking activity and behaviors by location. For example, the geolocation data allows for analysis of sleep, stress, and health (e.g., mental health) patterns for users in Alaska versus users located near the equator.

Geolocation data is created in the present invention using one or more hardware and/or software components. By way of example and not limitation, geolocation data is created using the Global Positioning System (GPS), low energy Bluetooth based systems such as beacons, wireless networks such as WiFi, Radio Frequency (RF) including RF Identification (RFID), Near Field Communication (NFC), magnetic positioning, and/or cellular triangulation. By way of example, geolocation data is determined via an Internet Protocol (IP) address of a device connected to a wireless network. A wireless router is also operable to determine identities of devices connected to the wireless network through the router, and thus is operable to determine the locations of these devices through their presence in the connection range of the wireless router.

In one embodiment, the mobile application is on a smartphone or a tablet. The mobile application is preferably operable to interface with a camera on the smartphone or the tablet. In one embodiment, the mobile application is operable to estimate gender, age, and/or body mass index (BMI) from a selfie taken with the camera. In another embodiment, the mobile application is operable to detect chronic disease, alcohol use, and/or evidence of smoking from the selfie. In yet another embodiment, the mobile application is operable to age progress an image. In still another embodiment, the mobile application is operable to detect an emotion from a facial expression in the selfie. The mobile application uses computer vision algorithms to perform facial analysis. In one embodiment, the mobile application uses the International Affective Picture System (TAPS) to determine a user's emotion. Examples of facial analysis software are disclosed in U.S. Pat. Nos. 9,646,046, 9,317,740, 9,311,564, 9,177,230, 9,152,845, 9,147,107, 9,008,416, 8,913,839, 8,818,111, 8,780,221, 8,705,875, and 8,676,740 and U.S. Publication Nos. 20170105568, 20140242560, and 20130158437, each of which is incorporated herein by reference in its entirety.

In another embodiment, the mobile application is operable to recognize an emotion based on a user's voice. Examples of voice analysis software are disclosed in U.S. Pat. Nos. 9,786,299, 8,965,770, 7,940,914, 7,451,079, and 7,340,393 and U.S. Publication Nos. 20180005646 and 20150310878, each of which is incorporated herein by reference in its entirety.

In still another embodiment, the mobile application is operable to educate a user. In one embodiment, the mobile application is operable to incorporate data from at least one genetic test (e.g., ANCESTRYDNA, 23ANDME). Based on the at least one genetic test, the mobile application is operable to inform a user about health habits (e.g., diet, supplements) that will optimize the user's future health. In one example, the mobile application advises a user that a lack of sleep, too much stress, and the results of the at least one genetic test indicate that the user is predisposed to diabetes and/or autoimmune disorders.

The mobile application is also operable to manage exchanges between a user and their environment. In one example, the mobile application notes that the user's commute time is negatively impacting their stress level. In another example, the mobile application notes that interaction with an individual raises their stress level (e.g., toxic relationship). In yet another example, the mobile application is operable to detect a negative impact of social media use on the user. The mobile application advises a user to minimize time on social media due to the negative impact (e.g., measured through stress responses by the EDA and/or heart sensors). The mobile application preferably identifies these exchanges and coaches the user to minimize stress. The mobile application is also operable to identify positive influences. In one example, the mobile application identifies at least one individual that positively impacts a user's stress level. When the user is stressed out, the mobile application suggests that the user contact the at least one individual for support.

In yet another embodiment, the system is a decentralized platform utilizing blockchain technology. The decentralized platform is operable to store information regarding the user's health, sleep, and stress levels. In one embodiment, the data blocks within the chain are encrypted using cryptography. Individual users are able to grant access to their data by providing another individual (e.g., healthcare provider) with a private password or key. In one embodiment, the cryptography is symmetric cryptography. Symmetric cryptography uses a single key to both encrypt and decrypt data. More preferably, the cryptography is asymmetric cryptography. Asymmetric cryptography uses keypairs consisting of a public key and a private key. A public key is visible to everyone, but no actions on the user's account can be made using the public key. The private key is not publicly available, and is necessary to authorize any action on the user's account. In yet another embodiment, the asymmetric cryptography includes digital signatures. The digital signature provides integrity and are incorruptible. The blockchain-based decentralized platform provides security for peer-to-peer sharing of medical information by preventing unauthorized access to the user's private medical information.

As previously stated, the user is able to grant access to their data to third parties (e.g., healthcare provider, psychologist, nutritionist, fitness coach, researchers). In one embodiment, the system allows the user to be compensated (e.g., micropayments) for sharing the user's data. In another embodiment, the system provides information to the user regarding clinical trials for medical conditions. In yet another embodiment, the system allows researchers to initially screen users to determine if a user is potentially eligible for a clinical trial. The system also allows insurance companies and/or employers to reward users for positive behaviors (e.g., sleep goals, nutrition goals, fitness goals).

Health Data Exchange Platform

Health is no longer a local problem. People move freely and so does disease. Healthcare for the bottom of the economic spectrum around the world is currently not equal to the rest, but access to the internet and smartphones is moving faster than the speed of hospital and healthcare institutions. The more data that is shared, the better it is for consumers and medical advancement in society. Consumer driven healthcare is the path to decrease healthcare costs and reduction in chronic disease. By focusing on prevention, stress reduction, and sleep, consumers can eliminate going to the doctor as frequently. However, the key to separating the consumer from the doctor's office and to creating a health prevention system is to give health data rights back to consumers and create incentives for consumers to share their health data.

On one side, consumers give their sleep, fitness, and other general health data to companies that are tracking their health for free. Companies benefit from the use of the collected health data in company valuations and for profit. Consumers need better protection from companies who use their data for free. On the other side, some health-related data is valuable for certain research topics, but is never collected from consumers or shared for research and development purposes.

The present invention provides a health data exchange platform aiming to solve the above-mentioned problems. The health data exchange platform of the present invention enables live database interactions, massive data integration, and target population identification, and prompts better awareness, habits, and responses with incentives. Genetic information, testing results, chronic problems, drug interactions, and all types of health-related data from consumers from varied backgrounds are aggregated by the health data exchange platform. Consumers own the health-related data generated from and by them and are incentivized by the health data exchange platform to share their data with interested parties. The health data exchange platform helps improve overall consumer health conditions, and advances medical diagnosis and research which will eventually benefit consumers and the general population in human society as a whole. The health data exchange platform keeps data on one platform that all health interchanges are operable to interact with and the user gets personalized care for their specific body.

A distributed ledger is a database of replicated, shared, and synchronized digital data based on consensus algorithms across a peer-to-peer network. Blockchain is a distributed ledger secured by cryptography and managed via a consensus algorithm on a peer-to-peer network. In one embodiment, the health data exchange platform is built based on distributed ledger technology. In one embodiment, the health data exchange platform is blockchain-based.

In one embodiment, the health data exchange platform is a public blockchain platform. In one embodiment, the public-blockchain-based health data exchange platform is built on an existing public blockchain platform (e.g., the Bitcoin blockchain, the Ethereum blockchain, etc.). In one embodiment, the public-blockchain-based health data exchange platform is built as a new public blockchain.

In another embodiment, the health data exchange platform is a global, distributed, append-only public ledger. One example of a global, distributed, append-only public ledger is disclosed in U.S. Pat. No. 9,635,000, which is incorporated herein by reference in its entirety. An identity is created for each individual and/or entity. The identity is preferably validated by the health data exchange platform. In one embodiment, a login PIN/password (e.g., 20 alphanumeric characters and/or symbols) is used to enroll in and/or access the health data exchange platform. Alternatively, a unique image is used to enroll in and/or access the health data exchange platform. In still another embodiment, biometric data (e.g., facial features, fingerprints, voices, heartbeats, vein recognition) is used to enroll in and/or access health data exchange platform.

Preferably, in another embodiment, the health data exchange platform is a private blockchain platform. Only permissioned users are allowed to make transactions on the private-blockchain-based health data exchange platform. In one embodiment, the private-blockchain-based health data exchange platform is built on an existing public blockchain platform (e.g., the Bitcoin blockchain, the Ethereum blockchain, etc.). In one embodiment, the private-blockchain-based health data exchange platform is built as a new private blockchain.

Figure 4:
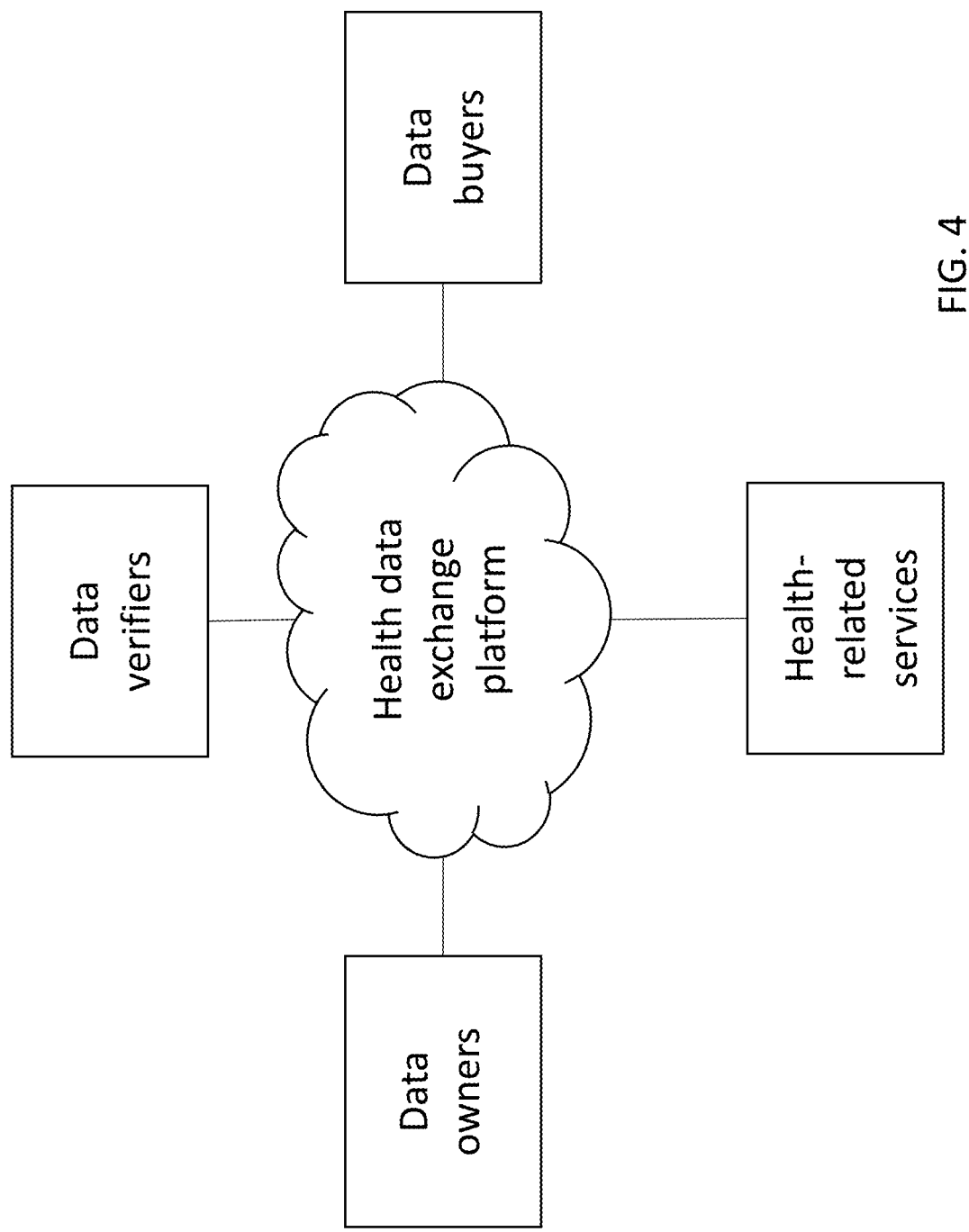
FIG. 4 illustrates one embodiment of a blockchain-based health data exchange platform.

FIG. 4 illustrates one embodiment of a blockchain-based health data exchange platform. Users on the blockchain-based health data exchange platform include data owners (e.g., consumers, patients, etc.) and data buyers (e.g., commercial companies, academic institutions, independent researchers, etc.). Data owners and data buyers make transactions directly on the blockchain-based health data exchange platform without an intermediary. In one embodiment, users on the blockchain-based health data exchange platform further includes data verifiers (e.g., physicians, government agencies, etc.) who provide verification for health data from data owners. In one embodiment, users on the blockchain-based health data exchange platform further include third-party service providers (e.g., medical billing companies, insurance companies, drug providers, etc.).

In one embodiment, health data include medical history records, real-time biometric data, sleep data, fitness data, workout data, genomic data, identity-related data, historical subjective data, historical objective data, etc. For example, but not for limitation, the medical history records include information related to illness and disease, lab data, and family medical history; the real-time biometric data includes information from the body sensors (e.g., pulse rate, heart rate, hydration, body temperature, etc.); the sleep data includes total sleep time, time spent in REM, time spent in deep sleep, time to sleep onset, waking time, etc.; the fitness data includes BMI, bone density, etc.; the workout data includes exercise types, exercise frequencies, exercise time (e.g., hours in the morning, afternoon, or evening), exercise length, exercise location, etc.; the genomic data includes commercial and/or lab DNA testing and sequencing data; and the identity-related data includes age, gender, race, geographical location, etc.

In one embodiment, health data is recorded on the blockchain-based health data exchange platform and accessible by authorized users. In one embodiment, health data is entered or loaded manually to the blockchain-based health data exchange platform for recordation by data owners via a user device in network communication with the blockchain-based health data exchange platform. In another embodiment, health data is automatically collected and transmitted by one or more authorized data capture device to the blockchain-based health data exchange platform for recordation via network communication. For example, but not for limitation, the one or more authorized data capture device is at least one wearable including application programs for sleep tracking, workout tracking, fitness tracking, etc.

In another embodiment, the health data is stored off-chain. For example, but not for limitation, the health data is stored locally at a network-attached storage. Also, for example, but not for limitation, the health data is stored on a third-party cloud platform. When there is a transaction request, a data owner is able to transmit related health data to a data buyer via network communication, and the transaction is recorded on the blockchain-based health data exchange platform.

Data verifiers have limited authority upon health data. For example, doctors or physicians are authorized to verify a user's medical history records based on zero-knowledge proof, but not authorized to make transactions of the health data. The FDA preferably has authority to approve certain devices and application programs for health monitoring or diagnostic purposes, but is not authorized to make transactions of the health data.

In one embodiment, the health data is formatted and stored with a certain standard. For example, but not for limitation, the health data is formatted and stored with Fast Healthcare Interoperability Resources (FHIR) standard for interoperability. In one embodiment, the health data is encrypted and secured with a cryptography algorithm. For example, a public/private key pair is generated for at least one portion of the health data for a user. When a transaction occurs, data buyers are authorized to access the at least one portion of the health data with the private key.

A smart contract is a computer protocol intended to digitally facilitate, verify, or enforce the negotiation or performance of a contract. In the context of blockchain, smart contracts are self-executing codes on a blockchain that automatically implement the terms of an agreement between parties.

Figure 5:
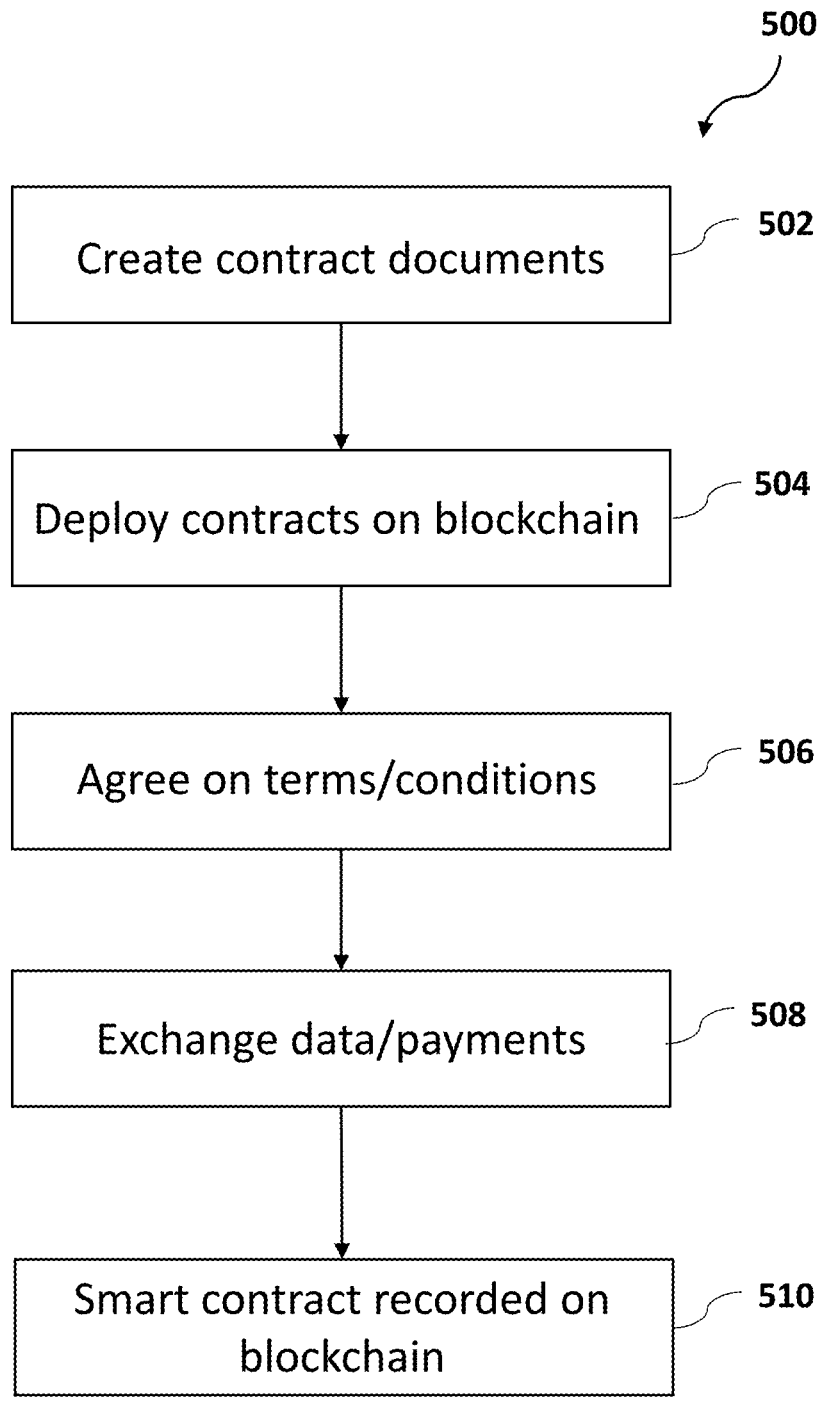
FIG. 5 illustrates one embodiment of a method for implementing smart contracts on the blockchain.

In one embodiment, smart contracts are implemented for data transactions on the blockchain-based health care data exchange platform. One method for implementing smart contracts on the blockchain 500 is shown in FIG. 5. Data agreements, terms and conditions, consent forms, and other related documents by both a data owner and a data buyer are operable to be programmed to a smart contract in step 502. A smart contract is deployed between the data owner and the data buyer on the blockchain in step 504. After the smart contract is deployed on the blockchain, both the data owner and the data buyer review all related documents and agree with all the terms and conditions in step 506. The data owner transmits health data to share with the data buyer in step 508. In one embodiment, the data owner is compensated by sharing the health data in step 508. Thus, a smart contract between the data owner and the data buyer is recorded on the blockchain-based health data exchange platform in step 510. The data buyer is then able to access the health data using a third-party device. Data transactions are timestamped, immutable, and auditable on the blockchain once executed.

Every smart contract has a unique identifier. In one embodiment, the unique identifier is a hash value generated by a hash algorithm in the blockchain. In another embodiment, the unique identifier is generated by another mathematical algorithm (e.g., mathematical formulation of quantum mechanics).

In another embodiment, the health data exchange platform allows a user to specify permissions for the health data. In one embodiment, the permissions extend to any data buyer who meets the terms and conditions. For example, a first data buyer is a research institution and offers to pay $25 for specific health data from a user. If a second data buyer is also a research institution and offers to pay $25 for the specific health data, a smart contract is automatically executed between the second data buyer and the user. However, if a third data buyer is not a research institution, requests different data, and/or does not offer at least $25, the user must review the new terms and conditions.

In one embodiment, the blockchain-based health data exchange platform enables micropayments between data buyers and data owners. Data owners and data buyers each have a digital wallet for transactions. In one embodiment, the micropayments are in the form of fiat currency, credits, and/or cryptocurrencies. For example, but not for limitation, accepted cryptocurrencies include bitcoin, ethers, etc. In one embodiment, the blockchain-based health data exchange platform issues its own cryptocurrency or token for data exchange.

In one embodiment, the blockchain-based health data exchange platform provides SDK and APIs for decentralized application program (dApps) development.

Data owner privacy is protected on the blockchain-based health data exchange platform. The health data shared with data buyers are encrypted for transmission and access, only authorized users are allowed to access but not allowed to share with other users. On the other hand, personally identifiable information is pre-vetted from the health data so that data owner identity is not leaked. Certain data of interest are operable to be disclosed on the blockchain-based data exchange platform for advertisement without disclosing data details or personal identity, for example but not for limitation, diseases, rare gene variants, race categories, age ranges, and/or geographical regions.

The blockchain-based health data exchange platform provides data ownership and access rights to users from whom the health data is generated, and incentivizes data owners to collect and share data with data buyers for health and disease related research and product developments. Health data storage is also decentralized and data security is enhanced to prevent data breach and other malicious attacks.

In one embodiment, the blockchain-based health data exchange platform enables self-insured companies to negotiate healthcare costs by tracking health data from members. The self-insured company is operable to encourage healthy behaviors from members with health credits or cryptocurrencies on the blockchain-based health data exchange platform. The health credits are operable to be redeemed towards other needs on the blockchain-based health data exchange platform. Conventional insurance companies also benefit from the blockchain-based health data exchange platform by tracking health data from insured individuals and encouraging healthy behaviors with health credits.

In one embodiment, the blockchain-based health data exchange platform assists medical research and/or clinical trials. The blockchain-based health data exchange platform enables researchers to contact and recruit subjects for studies based on public data owner information on the platform. The blockchain-based health data exchange platform also enables data buyers such as researchers to advertise research projects or clinical trials to attract data owners. For example, a data owner with a rare disease or an incurable one is enabled to find a clinical trial for the latest treatment. Also, for example, a menopause study is able to contact and recruit users via the blockchain-based health data exchange platform based on the public data owner information. Currently many research projects and clinical trials tends to be limited to subjects from a certain geographical area or even a certain social economic group. The blockchain-based health data exchange platform enables researches and trials to reach more people from various regions and with diverse social economic backgrounds. Payments and anonymity are based on contracts between the research projects/clinical trials and subjects.

Advantageously, the blockchain-based health data exchange platform broadens genetic testing and diversifies available genomic data because consumers are incentivized to get genetic testing and share their genomic data. In one embodiment, genetic testing is done by a commercial company (e.g., 23ANDME), but genomic data is owned by users for whom the genetic testing is done. In one embodiment, genomic data is stored in a genomic database owned by the commercial company but controlled by genomic data owners. The genomic database is interoperable with the blockchain-based health data exchange platform, and genomic data owners are able to share their genomic data via the blockchain-based health data exchange platform. In another embodiment, genomic data owners store their genomic data at a local database or a cloud platform operable for communication with the blockchain-based health data exchange platform. Genomic data are valuable in providing insights into personal health and enabling data-drive choices for disease prevention, medication, diet, exercise, and even family planning.

In one embodiment, the blockchain-based health data exchange platform enables long term studies for chronic diseases. Health-related habits, behaviors, stress, sleep, and other health-related data are tied together via the blockchain-based health data exchange platform and provide a better picture of how a disease evolved.

In one embodiment, the blockchain-based health data exchange platform facilitates various public health initiatives. For example, feedback on use, efficacy, and population density of vaccination from the blockchain-based health data exchange platform helps to determine risks for outbreaks.

User Profile and Interactions

Although there are currently systems to protect, manage, and trade information (e.g., social, medical) about individuals, the present invention combines the data signature for an individual with a genotype and a phenotype of the individual. A user profile of the individual is defined using the genotype and the phenotype. Tying the user profile to the genotype and the phenotype assists in making the individual unique and provides additional protection for the digital identity of the user. The user profile preferably also includes purchase history, social media history, web browsing history, and/or data from sensor technology. In one embodiment, the user profile includes biodata, sleep data, stress information, medications, supplements, disease profile, genotypes, workout information, diet information, social behaviors, emotional data, cognitive pursuits, data from third party health applications (e.g., APPLE HEALTH, GOOGLE HEALTH), how often the user interacts with the database (e.g., the health data exchange platform, phenotype network), hobbies, group memberships, and/or interests.

Traditional forms of identification include name, address, date of birth, and government issued identification numbers (e.g., Social Security Number, driver's license number). Medical services currently use these traditional forms of identification. As wearables (e.g., APPLE WATCH, SAMSUNG GALAXY WATCH, FITBIT, OURA), digital bioinformation, and third-party services (e.g., APPLE HEALTH) become more popular, user identification needs to be redefined to include these new methods of identification.

The health data exchange platform is preferably operable to group users by phenotypes and/or genotypes. For example, a user with a wearable device (e.g., APPLE WATCH) wants to engage with other users that have similar health and/or fitness goals. The user wants to attend the same gym or fitness class, hike at the same location, go to the same dog park, etc. as the other users with similar goals. Although there is a social component, the connection between users is driven by the health goal. Age, weight, gender, and/or current disease phenotype ontology serve as a starting point and combine with the user profile to create suggestions on health, life, behavioral, emotional, and cognitive choices. This provides a feedback loop to the user.

In one example, a 34-year old female lives in Charlotte, N.C. She has two kids, and uses an APPLE WATCH with APPLE HEALTH. She attends a gym, commutes 30 minutes each day, and has poor quality sleep for 6-7 hours each night. Although she does not currently have health problems now, she has a family history of diabetes and has not lost all of her pregnancy weight. Her husband then unexpectedly loses his job. The stress in this case will likely be intense for 6 months if her husband gets a job quickly and could potentially be longer if he remains unemployed for an extended period of time. This time frame is critical to prevent disease manifestation later. Recommendations of cognitive behavioral therapy (CBT), increasing sleep, and watching less television might help her prevent the stress from taking her genotype to a diseased phenotype. In a preferred embodiment, social media posts, digital signature, and biomarkers provide indicators that intervention is needed and why the intervention is needed. Without intervention, she will likely vent that stress in a way that is typical for her genotype. Interventions are personal, emotional, behavioral, medical, and/or social. The health data exchange platform creates constant feedback by searching and comparing similarities between users. This female is preferably grouped not only with the women she exercises with, but also grouped with other people who have had a spouse lose their job, short sleepers, and moms. Additionally, she is grouped by her ancestral genotype, recent bloodwork, heart rate variability (HRV) graph, etc. For example, if she has Chinese ancestry, she is more likely to respond to an intervention that provided a positive outcome to a female from China.

In another example, a user having a certain genotype is at high risk of a certain type of cancer. However, the environment around the user and their phenotype defines whether the user will actually get that cancer and when the user gets that cancer. Current studies work to eliminate outside variables and create a topography for a study that is most similar to what researchers are hoping to study, but conducting long-term studies and finding the exact genotype and phenotypes are difficult. Advantageously, the health data exchange platform provides the ability to perform multi-tier searches and find similar ancestry, genotypes, and phenotypes around the world.

Figure 6:
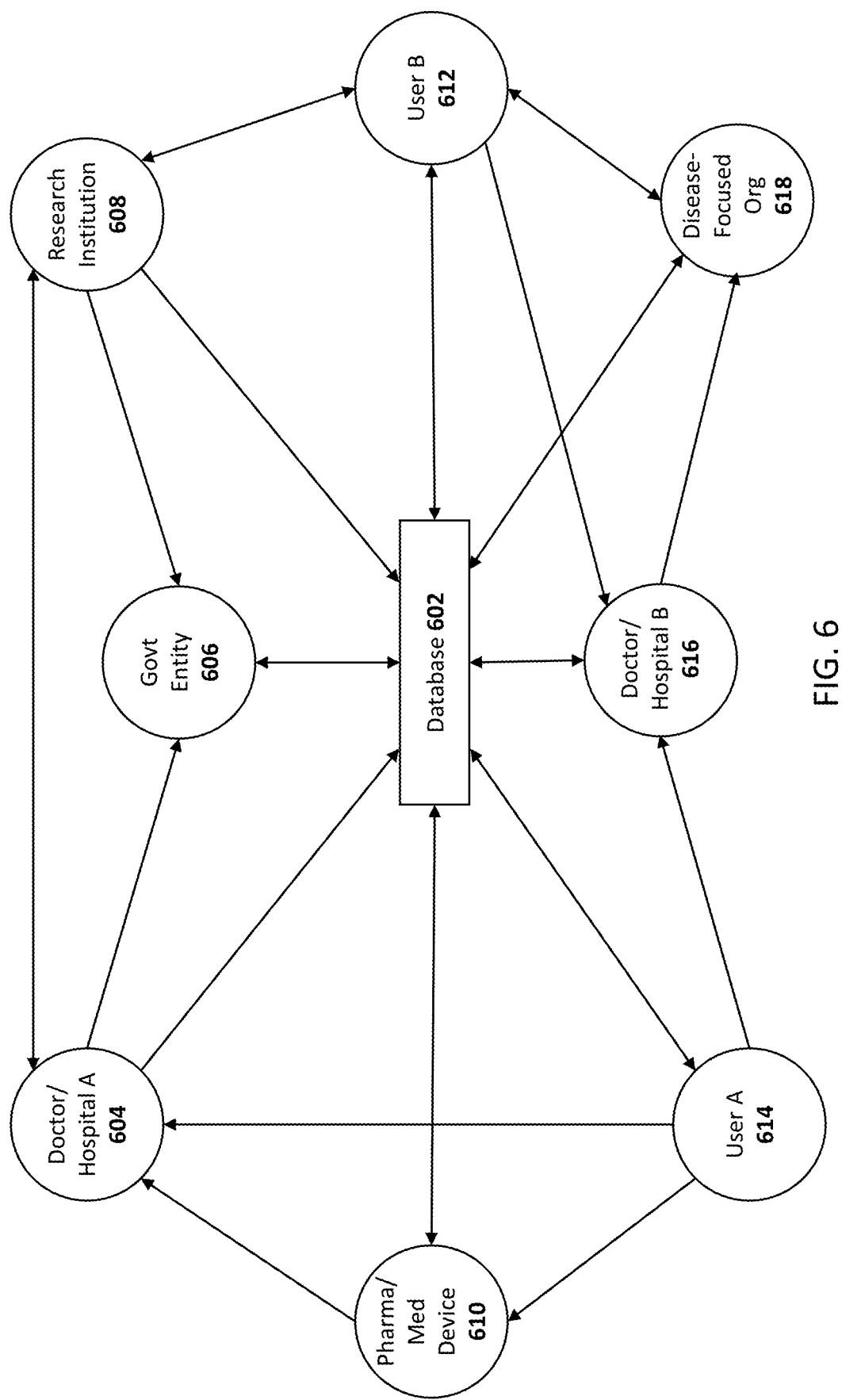
FIG. 6 is a block diagram illustrating one embodiment of interactions between users and entities within a health data exchange platform.

FIG. 6 is a block diagram illustrating one embodiment of interactions between users and entities within a health data exchange platform. A database 602 stores information (e.g., user identification) about all users and entities within the health data exchange platform. Doctor/Hospital A 604 and Research Institution 608 want to share data and subjects. Doctor/Hospital A 604 and Research Institution 608 need approvals from Governmental Entity 606 (e.g., Food and Drug Administration (FDA)). Doctor/Hospital A 604, Governmental Entity 606, Research Institution 608, Doctor/Hospital B 616, and Disease-Focused Organization 618 (e.g., cancer society, heart association) all provide information to the database 602. Pharmaceutical Company/Medical Device Manufacturer 610 wants doctors from Doctor/Hospital A 604 and Doctor/Hospital B 616 to prescribe their drugs or suggest their medical device. Research Institution 608 wants User B 612 to participate in a research study and User B 612 wants financial compensation. User A 614 and User B 612 send data to the database and set permissions for data usage. User A 614 and User B 612 receive information and tokens (e.g., payment, compensation) for sharing information. User A 614 wants to use a drug or medical device manufactured by Pharmaceutical Company/Medical Device Manufacturer 610. User A 614 checks in at Doctor/Hospital B 616 and wants a second opinion from Doctor/Hospital A 604. Pharmaceutical Company/Medical Device Manufacturer 610 sends tokens (e.g., payment, compensation) to Database 602 in exchange for information from the Database 602. Doctor/Hospital B 616 is affiliated (e.g., a doctor or employee serves as an officer) with Disease-Focused Organization 618. User B 612 checks in at Doctor/Hospital B 616. User B 612 wants additional information from Disease-Focused Organization 618. Governmental Entity 606 and Disease-Focused Organization 618 receive information from Database 602.

Figure 7:
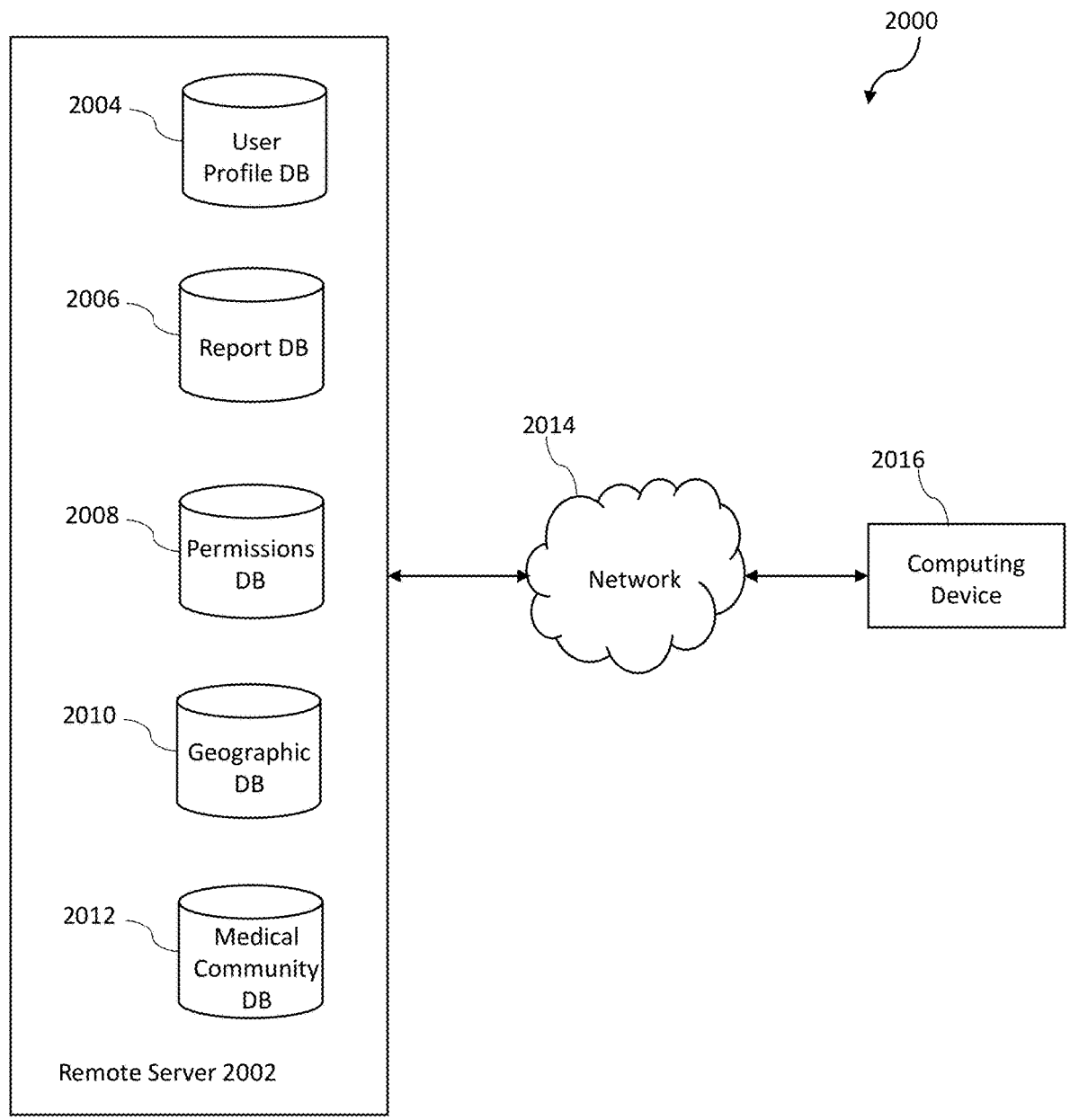
FIG. 7 is an example of a phenotype network.

In a preferred embodiment, the health data exchange platform includes a phenotype network. FIG. 7 is an example of a phenotype network 2000. The phenotype network includes at least one remote server 2002. The at least one remote server 2002 is preferably a plurality of distributed servers. The at least one remote server 2002 includes a user profile database 2004, a report database 2006, a permissions database 2008, a geographic incident database 2010, and a medical community database 2012. The user profile database 2004 stores information about users, including, but not limited to, social information, behavioral information, habit information, and user location. The report database 2006 stores health report information including, but not limited to, medical reports, sleep logs (e.g., time in bed, temperature of room, temperature of sleep surface or sleep blanket), wearable sensor data (e.g., sleep information, heart rate variability data), blood test results, and genetic testing data (e.g., 23ANDME). The permissions database 2008 stores information relating to what data each user has authorized to release to other entities (e.g., doctors, research institutions, companies). In a preferred embodiment, the phenotype network includes blockchain encryption. The permissions database 2008 stores links to where the permissible data is stored on the distributed ledger. The geographic database 2010 stores information regarding known geographical health issues by neighborhood, city, county, state, country, region, and/or zip code (e.g., water quality in Flint, Mich., cancer cluster in Woburn, Mass.). The medical community database 2012 includes information including, but not limited to, research studies, clinical trials, and/or disease information. Information stored on the at least one remote server 2002 is accessible over the network 2014 (e.g., cloud) via at least one computing device 2016 (e.g., smartphone, tablet, laptop computer, desktop computer).

Figure 8:
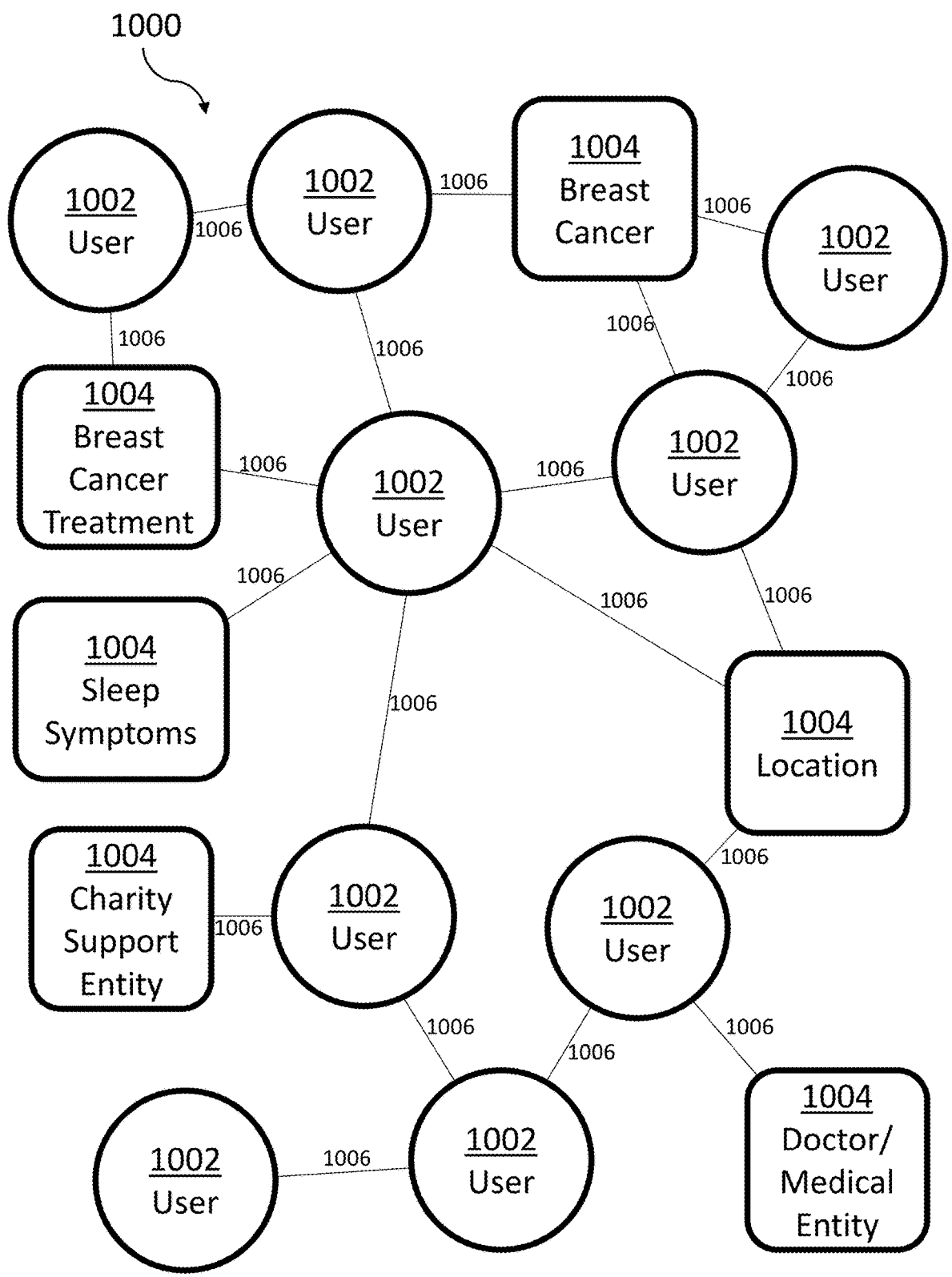
FIG. 8 illustrates an example of a phenotype graph.

FIG. 8 illustrates an example of a phenotype graph 1000. The example shown in FIG. 8 includes user nodes 1002, concept nodes or phenotype categories 1004 (e.g., breast cancer, breast cancer treatment, sleep symptoms, location, charity support entity, doctor/medical entity), and edges 1006 between nodes. Each node 1002, 1004 corresponds to a user, entity, phenotype category, concept, or digital presence. The edges 1006 represent connections between users, entities, concepts, and phenotype categories. In this graph, users are managing their way through breast cancer. Some users do not have breast cancer, but are connected closely to someone who does.

The nodes 1002, 1004 and the edges 1006 are operable to store or access information about a user. This express information about the user is still the property of the user. The health data exchange platform allows the user to digitally tag the information and put contract restrictions on the digital information. For example, the user indicates that a sleep sensor has shown them to be a short sleeper with a low deep sleep percentage. An entity (e.g., research institution, corporation) is then able approach the user to participate in a research study or try a product if the user has made that data public. Marketing companies are able to sell user fields and/or data when given permission by the user to do so. Another user in a similar phenotype is able to suggest a solution that worked for them.

Advantageously, the phenotype-based network provides better recommendations for users than social-based networks. Social networks tend to be geographically isolated. Users are often friends with individuals from work and/or school (e.g., college, high school). Social connections based on phenotyping expand social groups.

Figure 9:
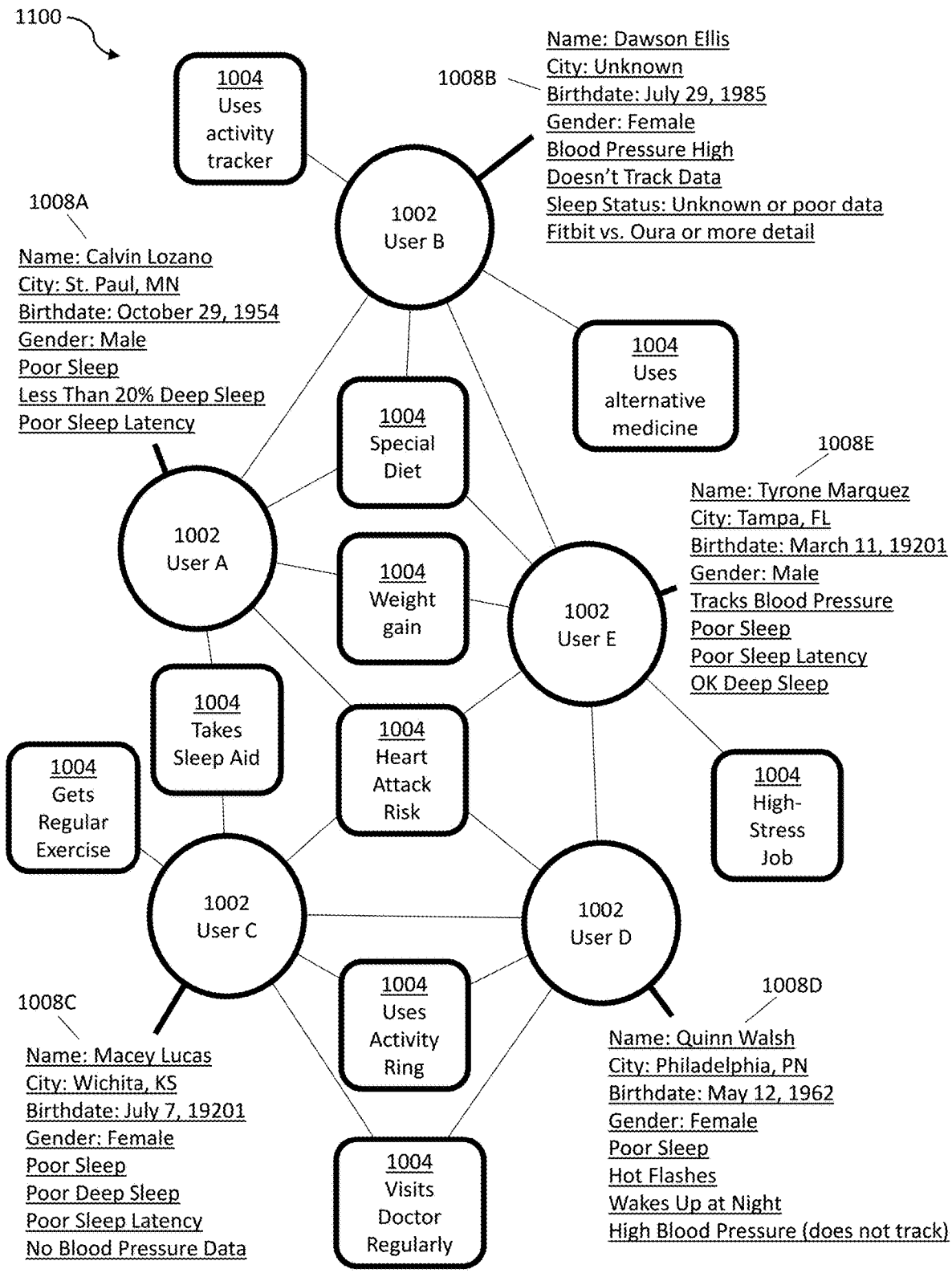
FIG. 9 illustrates a phenotype graph showing user profiles, user phenotypes, and missing phenotype information.

FIG. 9 illustrates a phenotype graph 1100 showing user profiles, user phenotypes, and missing phenotype information. The example shown in FIG. 9 includes user nodes 1002 (e.g., Users A-E), concept nodes or phenotype categories 1004 (e.g., uses activity tracker, uses alternative medicine, special diet, weight gain, heart attack risk, takes sleep aid, gets regular exercise, high-stress job, uses activity ring, visits doctor regularly), and user profiles 1008A-E. Each user profile 1008 preferably includes a name, a location, a birthdate, a gender, and health information (e.g., sleep information, blood pressure data).

Figure 10:
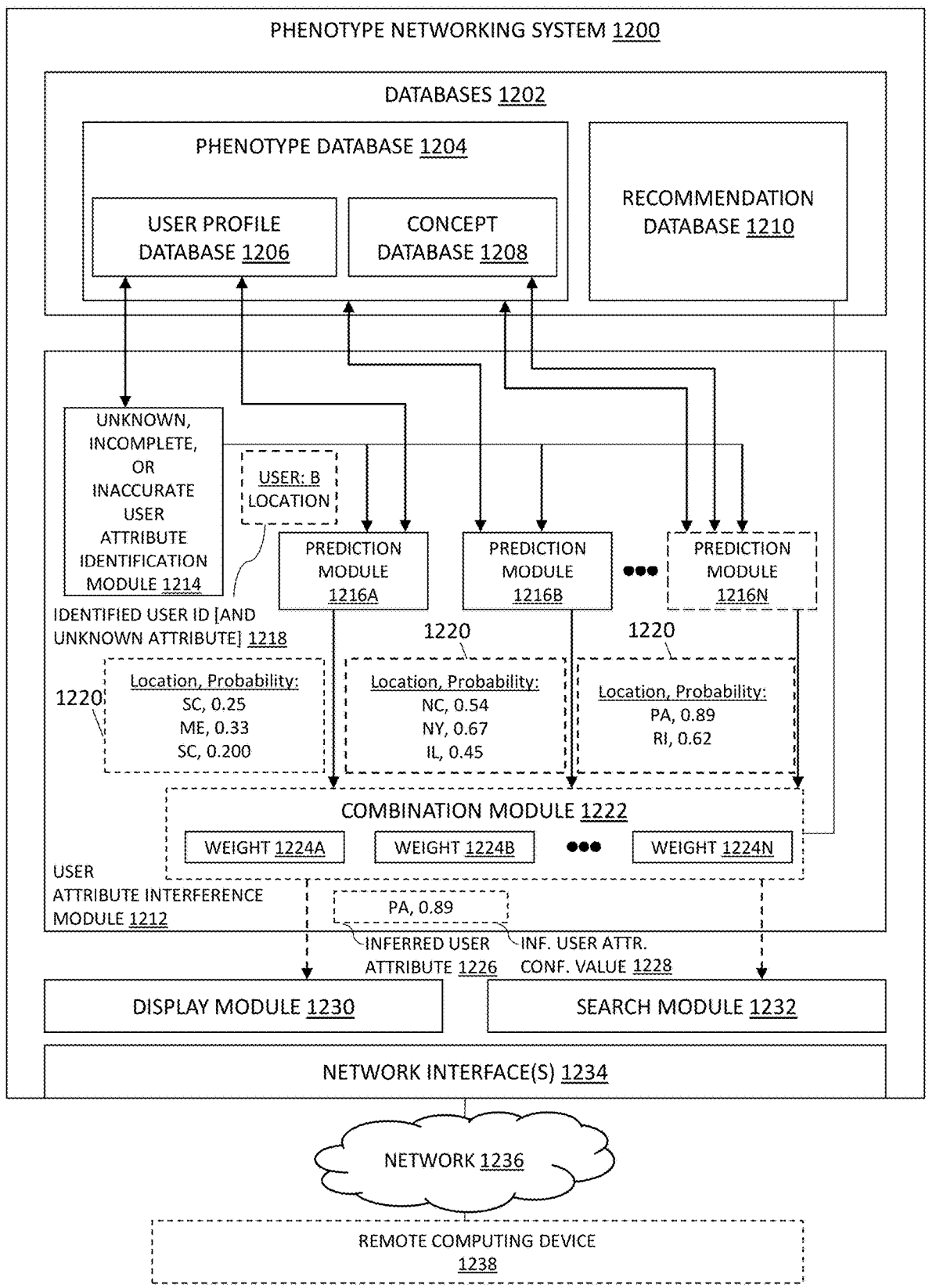
FIG. 10 is a block diagram of a phenotype networking system.

FIG. 10 is a block diagram of a phenotype networking system 1200. The phenotype networking system 1200 preferably includes at least one remote server connected to at least one computing device 1238 (e.g., smartphone, tablet, laptop computer, desktop computer) via network 1236 using at least one network interface 1234. The phenotype networking system 1200 includes at least two databases 1202. The at least two databases 1202 include a phenotype database 1204 and a recommendation database 1210. The phenotype database 1204 further includes a user profile database 1206 and a concept database 1208.

The phenotype networking system 1200 further includes a user attribute inference module 1212. The user attribute inference module 1212 includes an unknown, incomplete, or inaccurate user attribute identification module 1214, a plurality of prediction module 1216A-1216N, and a combination module 1222. The unknown, incomplete, or inaccurate user attribute identification module 1214 uses the phenotype database 1204 to determine an unknown, incomplete, or inaccurate user attribute for a particular user. In one embodiment, the unknown, incomplete, or inaccurate user attribute identification module scans the phenotype database 1204 to identify users missing a value for the user attribute. In the example shown in FIG. 10, User B is missing a location (e.g., state) in 1218. The unknown, incomplete, or inaccurate user attribute identification module 1214 sends information to a plurality of prediction modules 1216A-1216N. The value "N" indicates that any number of prediction modules are compatible with the present invention.

Each prediction module 1216A-1216N uses a different prediction algorithm to generate a set of one or more possible predicted values and a probability 1220. The prediction modules use the phenotype database, the user profile database, the concept database, and/or information from a plurality of nodes of the phenotype database 1204 to determine an algorithm.

The combination module 1222 uses a plurality of weights 1224A-1224N to analyze the probability lists 1220 and determine an inferred user attribute 1226 and an inferred user attribute confidence value 1228. In one embodiment, a display module 1230 shows the inferred user attribute 1226 and prompts the user to confirm the value. In another embodiment, the inferred user attribute 1226 is sent to a search module to allow the phenotype networking system 1200 to search for that result. In still another embodiment, the inferred user attribute 1226 is stored in one or more of the databases 1202 (e.g., user profile database 1206).

Figure 11:
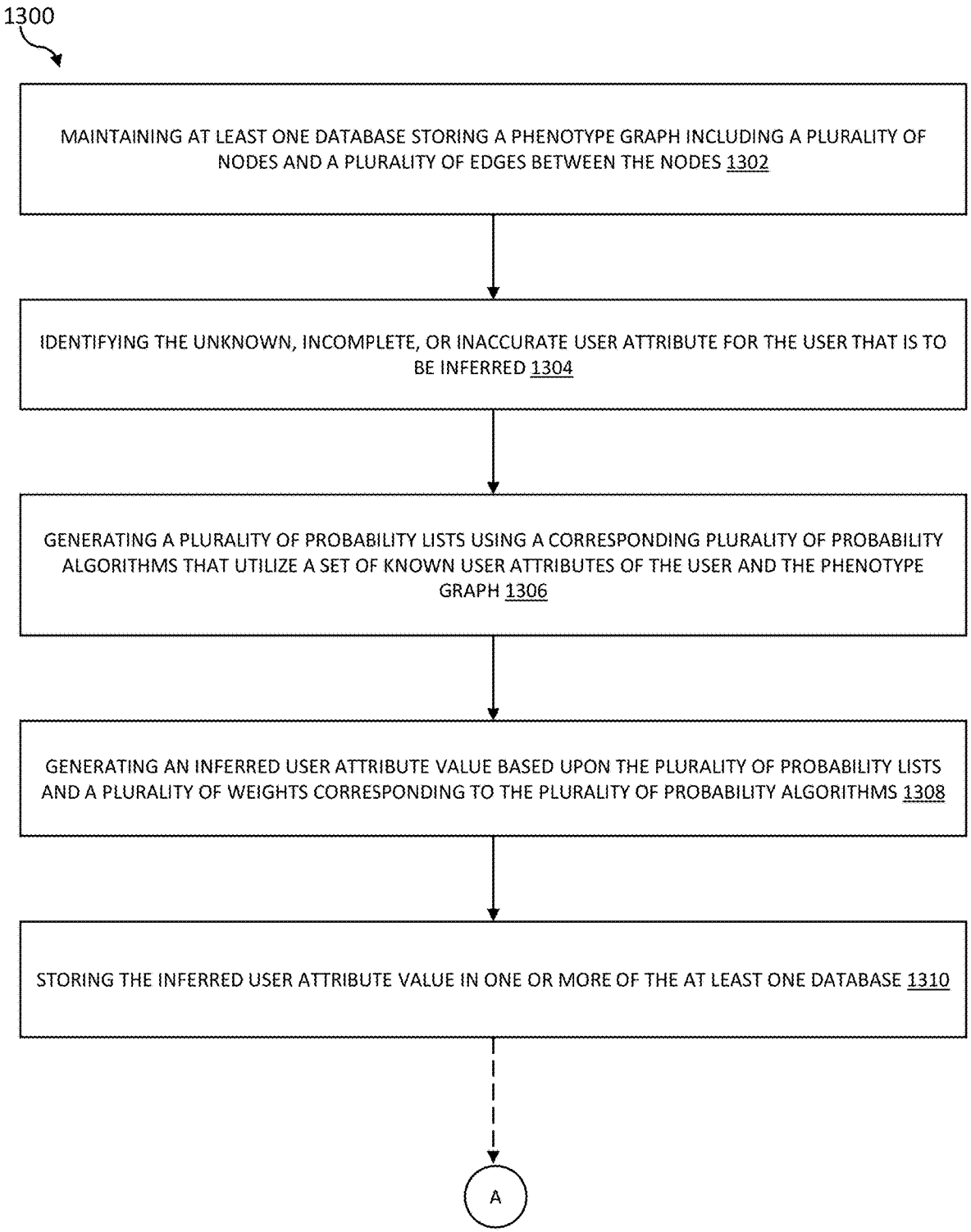
FIG. 11 is a flow chart illustrating one embodiment of a method for inferring unknown, incomplete, or inaccurate user attributes.

FIG. 11 is a flow chart illustrating one embodiment of a method 1300 for inferring unknown, incomplete, or inaccurate user attributes. At least one database is maintained that stores a phenotype graph that includes a plurality of nodes and a plurality of edges between the nodes in step 1302. The plurality of nodes includes user nodes and concept nodes or phenotype categories. The phenotype networking system identifies an unknown, incomplete, or inaccurate user attribute for a user that is to be inferred in step 1304. A plurality of probability lists is generated using a corresponding plurality of probability algorithms that utilize a set of known user attributes of the user and the phenotype graph in step 1306. Each probability list of the plurality lists includes a set of one or more probability entries that each include a prediction value and a confidence score corresponding to the prediction value. The prediction value is a possible value of the unknown, incomplete, or inaccurate user attribute. The confidence score is a value indicating a predicted likelihood that the prediction value is a correct value of the unknown, incomplete, or inaccurate user attribute. An inferred user attribute value is generated based on the plurality of probability lists and a plurality of weights corresponding to the plurality of probability algorithms in step 1308. Each weight of the plurality of weights indicates a relative confidence that the corresponding probability algorithm will generate a probability list including the prediction value that is the correct value of the unknown, incomplete, or inaccurate user attribute. The inferred user attribute value is stored in one or more of the at least one database in step 1310. In one embodiment, the method 1300 optionally continues to step A, which is described in FIG. 12.

Figure 12:
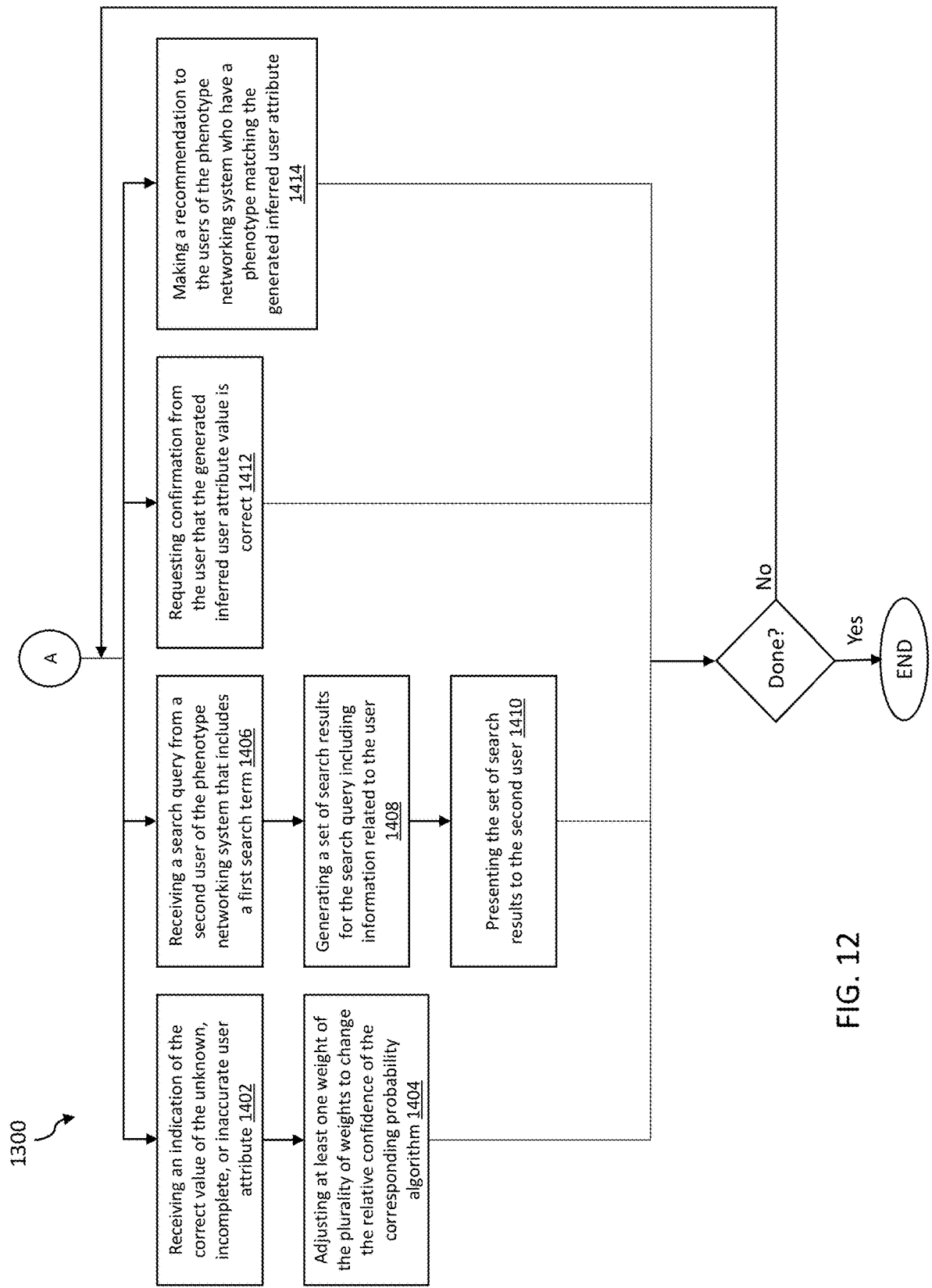
FIG. 12 is a flow chart illustrating optional steps of the method described in FIG. 11.

FIG. 12 is a flow chart illustrating optional steps of the method described in FIG. 11. Step A continues to step 1402, 1406, 1412, or 1414. Proceeding from step A to step 1402, the phenotype networking system receives an indication of the correct value of the unknown, incomplete, or inaccurate user attribute. The phenotype networking system adjusts at least one weight of the plurality of weights to change the relative confidence of the corresponding probability algorithm in step 1404. Proceeding from step A to step 1406, the phenotype networking system receives a search query from a second user of the phenotype networking system that includes a first search term. The phenotype networking system generates a set of search results for the search query including information related to the user in step 1408. The set of search results is presented (e.g., displayed on a user interface) to the second user in step 1410. Proceeding from step A to step 1412, the phenotype networking system requests confirmation from the user that the generated inferred user attribute value is correct. Proceeding from step A to step 1414, the phenotype networking system makes a recommendation to the users of the phenotype networking system who have a phenotype matching the generated inferred user attribute. Following steps 1404, 1410, 1412, or 1414, the phenotype networking system determines whether additional optional steps are required. If no additional optional steps are required, the method ends.

Figure 13:
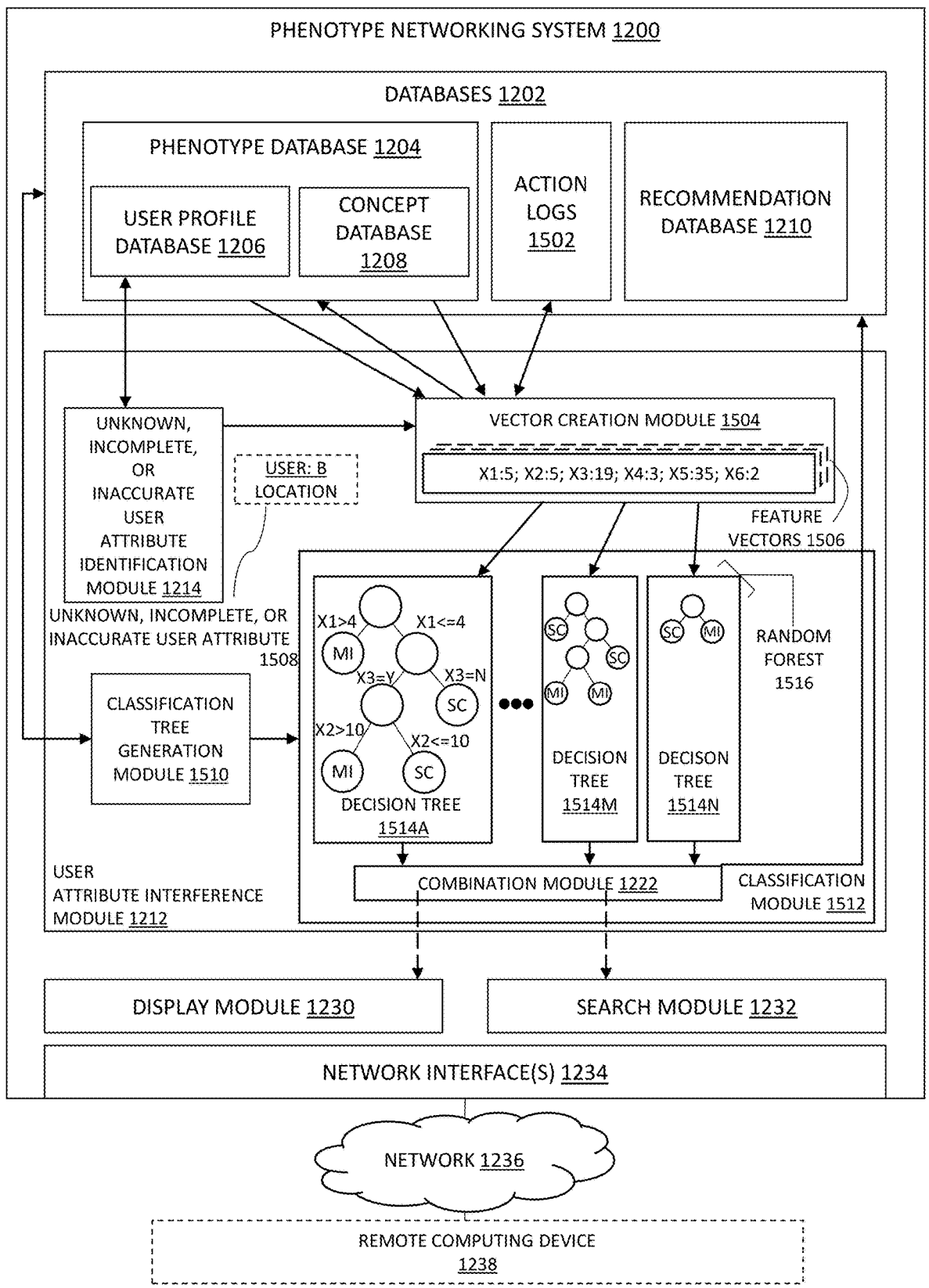
FIG. 13 illustrates a block diagram of one embodiment of a phenotype networking system for inferring user attributes using decision trees.

FIG. 13 illustrates a block diagram of one embodiment of a phenotype networking system for inferring user attributes using decision trees. The user attribute interference module 1212 of phenotype networking system 1200 includes a classification tree generation module 1510. The classification tree generation module 1510 generates at least one decision tree 1514A-1514N. Alternatively, the classification tree generation module 1510 generates a random forest classifier 1516. In yet another embodiment, classifiers include, but are not limited to, binary classifiers, mutliclass classifiers, linear classifiers, Naïve Bayesian classifiers, neural networks, Hidden Markov models, or support vector machines.

The phenotype networking system includes action logs 1502. The action logs 1502 record information including, but not limited to, a timestamp of when an action occurred, an identification of a user, an action type, an identification of where the action was directed (e.g., second user), and content associated with the action.

The unknown, incomplete, or inaccurate user attribute identification module 1214 uses the phenotype database 1204 of the databases 1202 to determine an unknown, incomplete, or inaccurate user attribute for a particular user. The unknown, incomplete, or inaccurate user attribute identification module 1214 scans the phenotype database 1204 to identify users without a value for the user attribute. In the example shown in FIG. 13, User B is missing a location identifier (e.g., state). A set of one or more feature vectors 1506 is created by a vector creation module 1504. The set of one or more feature vectors 1506 is sent to the decision trees 1514A-1514N. The decision trees predict a location (e.g., Michigan (MI), South Carolina (SC)). In one embodiment, the prediction also includes a confidence score for each prediction value.

The results from each of the decisions are input into the combination module 1222. The combination module 1222 determines a final inferred user attribute. In one embodiment, the final inferred user attribute is displayed on a display module 1230 (e.g., graphical user interface). In another embodiment, the display module prompts the user to confirm the final inferred user attribute. In yet another embodiment, the final inferred user attribute is sent to a search module 1232 to allow the final inferred user attribute to be searchable within the phenotype networking system. In still another embodiment, the final inferred user attribute is sent to one or more of the databases 1202 for storage (e.g., in user profile database 1206).

The phenotype network system is preferably operable to automatically suggest connections. This allows pertinent information to be shared with each phenotype. For example, users with breast cancer are grouped into a phenotype and information regarding a new breast cancer treatment is shared with the users in that phenotype. Users are able to belong to multiple phenotypes (e.g., breast cancer, moms, 40-45 years old). Further, candidates for connections are not limited to physical medical needs. Gifted children, parents of gifted children, caregivers, addiction groups, attention deficit hyperactivity disorder, people of specific ancestry (e.g., Irish), etc. are all phenotypes within the system.

Figure 14:
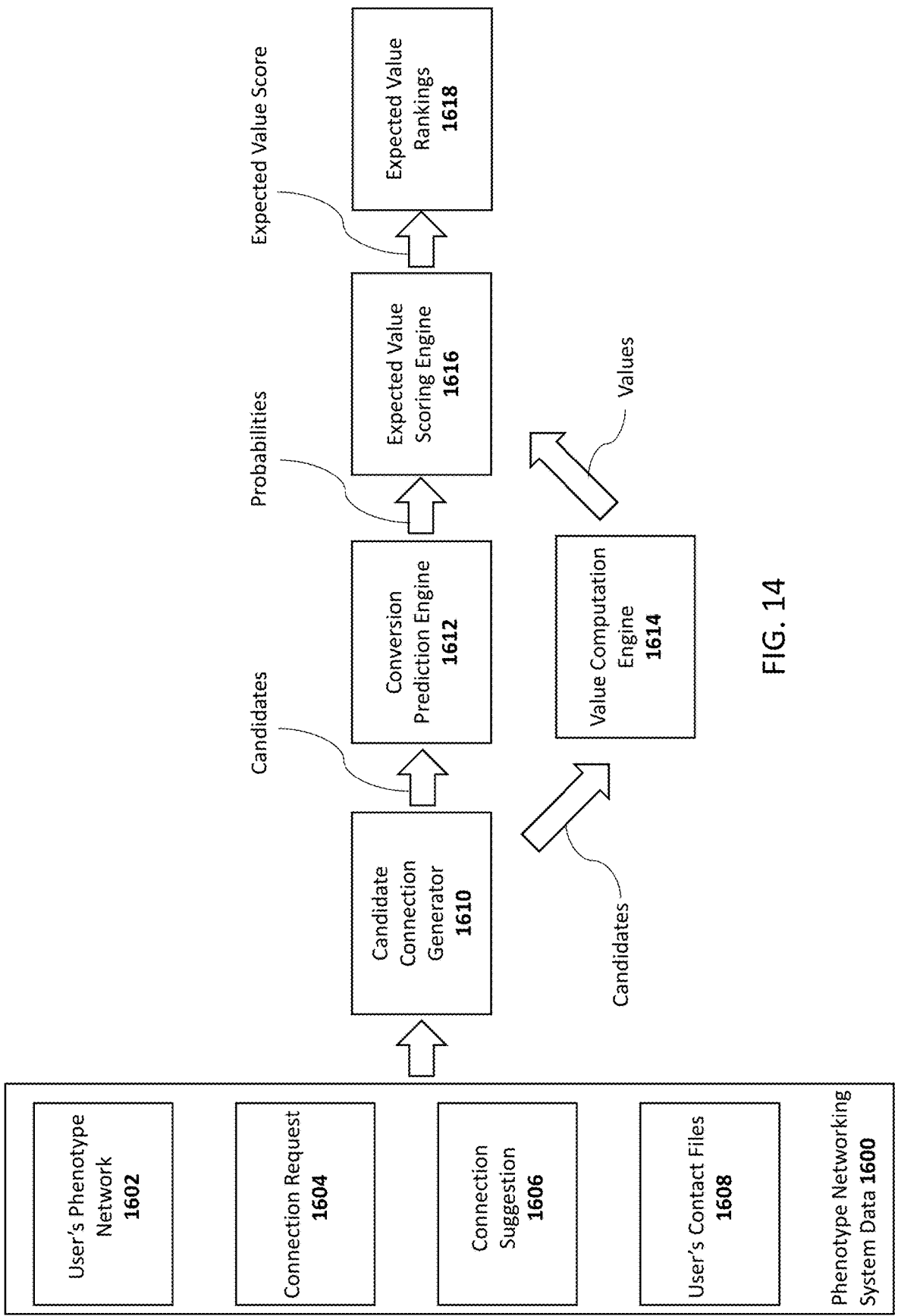
FIG. 14 illustrates a system for determining candidates for connections within the phenotype network system.

FIG. 14 illustrates a system for determining candidates for connections within the phenotype network system. The phenotype network system includes phenotype networking system data 1600, a candidate connection generator 1610, a conversion prediction engine 1612, a value computation engine 1614, an expected value scoring engine 1616, and expected value rankings 1618. The expected value rankings 1618 are preferably stored in a database. A candidate set of connections not currently associated with the user is generated by the candidate connection generator 1610 by accessing the phenotype networking system data 1600. The conversion prediction engine 1612 calculates the value to the phenotype networking system for the user and each candidate connection. The value computation engine 1614 calculates the value to phenotype networking system for each candidate connection if the user forms a connection with the user. The expected value scoring engine 1616 receives probabilities from the conversion prediction engine 1612 and values from the value computation engine 1614 to calculate an expected value score for each candidate connection. Each candidate connection is ranked in the expected value rankings 1618. Connections are suggested to the user via display, message, and/or other notification.

The phenotype networking system data 1600 includes the user's phenotype network 1602, connection request data 1604, connection suggestion data 1606, and the user's contact files 1608. The user's phenotype network 1602 includes, but is not limited to, connections with other users, phenotypes, medical entities, and/or health status. Connection request data 1604 includes information (e.g., names, entities, medical personnel) who have requested that the user add the connection to the user's phenotype network 1602. The connection suggestion data 1606 includes information (e.g., names, entities, medical personnel) who are suggested as connections by at least one of the user's current connections or the phenotype network system. The user's contact files 1608 include contact information (e.g., name, email address) of the connections the user has communicated with in the phenotype network system via email, direct message, text message, network feed, etc.

Figure 15:
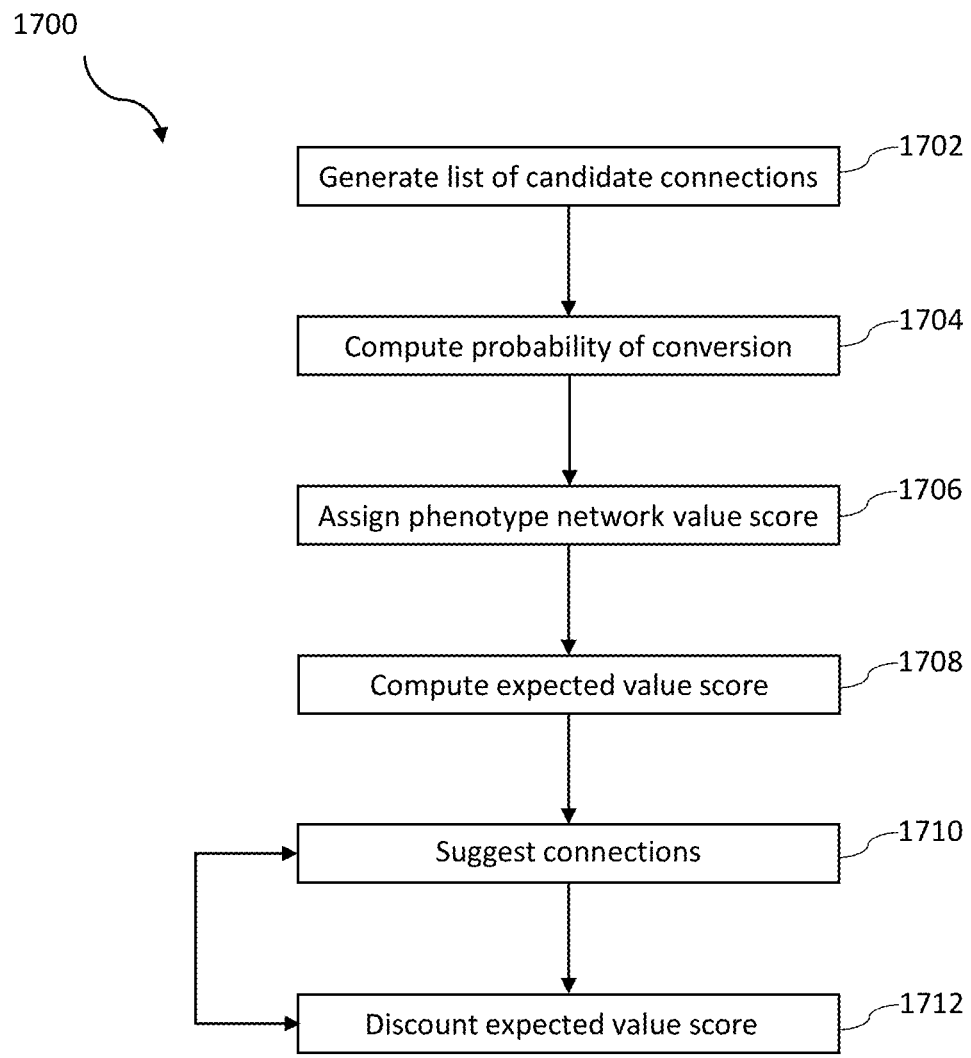
FIG. 15 illustrates one embodiment of a method to suggest connections within the phenotype network system.

FIG. 15 illustrates one embodiment of a method 1700 to suggest connections within the phenotype network system. For example, a user wants to find other users with a similar medical condition (e.g., breast cancer), a researcher wants to find subjects for a clinical trial, and a company wants to find users interested in a product. The method 1700 generates a list of candidate connections not currently associated with a user or an entity in step 1702. The method 1700 computes a probability of conversion to a connection in step 1704. The method 1700 assigns a phenotype network value score based on user preferences in step 1706. User preferences include, but are not limited to, race, age, disease, sex, and location. The phenotype network system is operable to allow users to personally weight phenotype qualities. An expected value score is computed in step 1708. The expected value score is a combination of the phenotype network value score and the probability of conversion. In one embodiment, the expected value score is computed by multiplying the phenotype network value score and the probability of conversion. Connections are suggested in step 1710 via display, message, and/or other notification. In one embodiment, suggested connections are above a threshold expected value score. If a connection is suggested multiple times in step 1710 without the user accepting the connection, the expected value score is discounted in step 1712. This is an iterative process.

Figure 16:
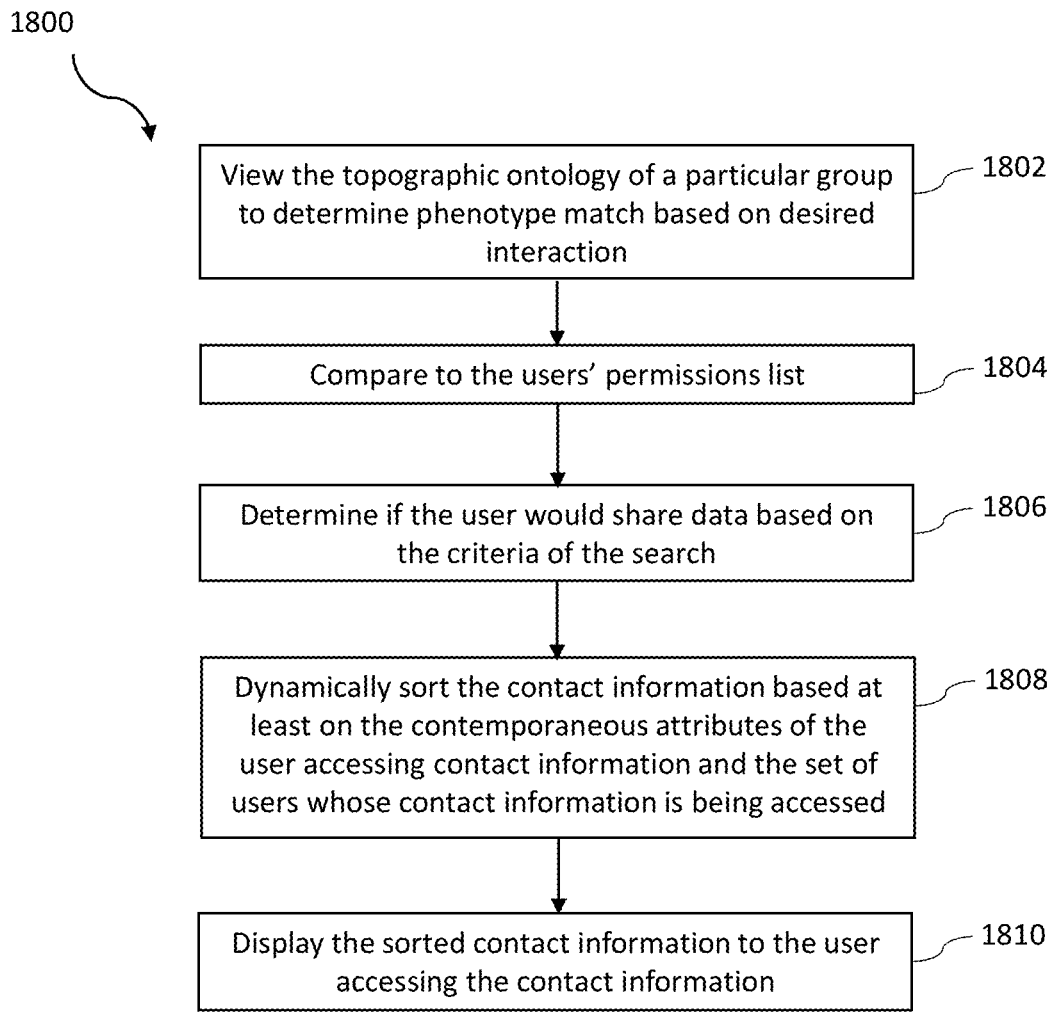
FIG. 16 illustrates a method of dynamically sorting information in the phenotype network system.

FIG. 16 illustrates a method 1800 of dynamically sorting information in the phenotype network system. The phenotype network system is operable to allow a user to view a topographic ontology of a particular group to determine a phenotype match based on a desired interaction (e.g., searching for users to be in a clinical trial based on disease and location) in step 1802. The phenotype network system compares the desired interaction to a permissions list of each user in step 1804. The phenotype network system determines if each user is willing to share data based on the criteria of the search in step 1806. The phenotype network system dynamically sorts contact information based at least on the contemporaneous attributes of the user accessing contact information and the set of users whose contact information is being accessed in step 1808. The phenotype network system displays the sorted contact information to the user accessing the contacting information in step 1810.

Figure 17:
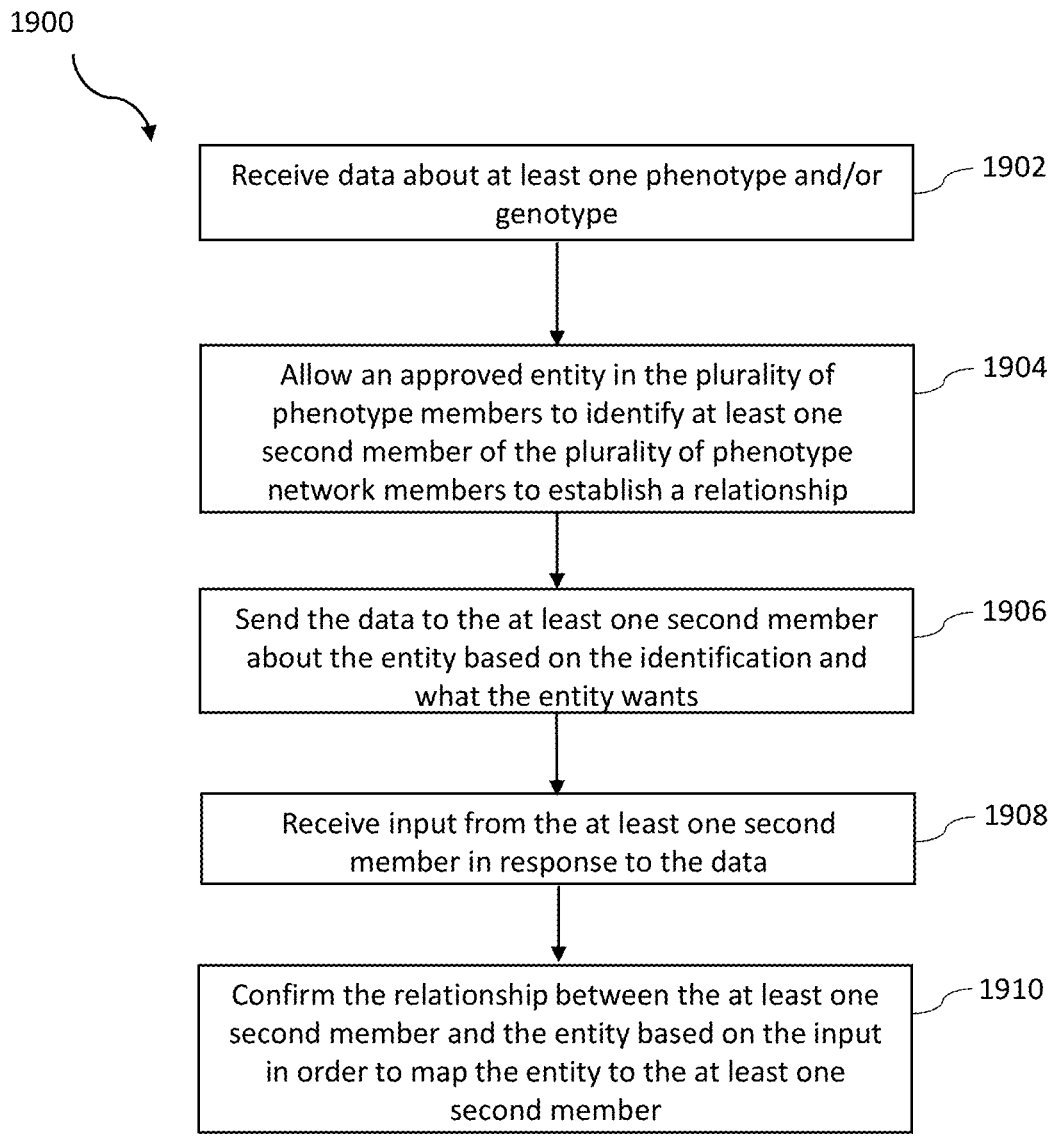
FIG. 17 illustrates one embodiment of a method for phenotype mapping in a phenotype network.

FIG. 17 illustrates one embodiment of a method 1900 for phenotype mapping in a phenotype network. Data about at least one phenotype and/or at least one genotype is received in step 1902. An approved entity (e.g., research institution, drug company, doctor, hospital, disease focused organization) in the plurality of phenotype members is allowed to identify at least one second member of the plurality of phenotype network members to establish a relationship in step 1904. Data is sent to the at least one second member of the plurality of phenotype network members about the entity based on the identification and what the entity wants in step 1906. Input is received from the at least one second member in response to the data provided by the entity in step 1908. In step 1910, the relationship between the at least one second member and the entity is confirmed based on the input in order to map the entity to the at least one second member. In one embodiment, the phenotype network system prompts the at least one second member to review privacy settings relating to the entity.

In one embodiment, the phenotype network system is operable to automatically tag users for multiple phenotype and genotype fields. For example, a white male user in a predominantly white community is prompted to automatically tag and/or fill information based on pictures, information from the community, and the user's digital footprint.

In another embodiment, the phenotype network system is operable to dynamically make recommendations (e.g., treatments, immunizations, phenotype, genotype) based on data including, but not limited to, social interactions, location data, biometric data (e.g., wearables), digital footprint (e.g., websites visited, search history, purchase history), and/or device usage (e.g., smartphone, tablet).

The phenotype network system preferably includes a graphical user interface (GUI). In one embodiment, the phenotype network system is operable to allow a user to select a profile picture, an avatar, or other image representation via the GUI. The GUI allows the user to set permissions for data within the phenotype network system. For example, the GUI allows the user to set permissions for sharing social information, behavioral information, phenotype, location data, genotype, disease ontology, etc. The GUI allows the user to set permissions for which data can be accessed, who can access the data (i.e., which connections), and what purposes the data can be accessed.

In a preferred embodiment, the phenotype network system propagates scores across a phenotype graph to identify users that possess data and/or phenotypes associated with a desired interaction. Examples of scoring information are found in U.S. Pat. No. 8,311,950, which is incorporated herein by reference in its entirety. In social networks, scores are generally weighted by likes or reviews. In contrast, scores in the phenotype network system are based on supply and demand of the medical information. A user in the phenotype network system is rewarded with offers for tokens, information, or other interactive engagements instead of likes as in a social network.

Figure 18:
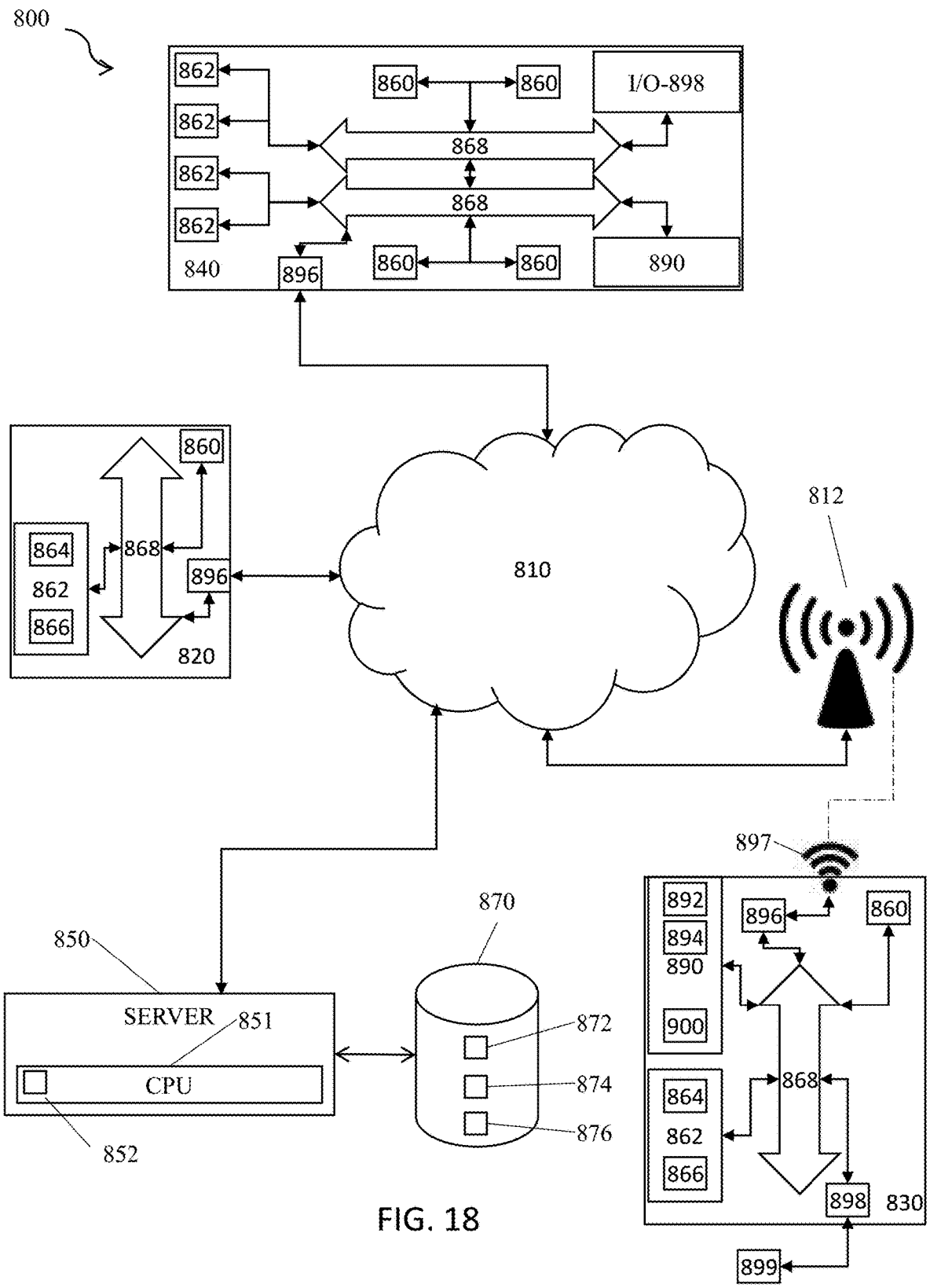
FIG. 18 shows a schematic diagram illustrating general components of a cloud-based computer system.

FIG. 18 is a schematic diagram of an embodiment of the invention illustrating a computer system, generally described as 800, having a network 810, a plurality of computing devices 820, 830, 840, a server 850, and a database 870.

The server 850 is constructed, configured, and coupled to enable communication over a network 810 with a plurality of computing devices 820, 830, 840. The server 850 includes a processing unit 851 with an operating system 852. The operating system 852 enables the server 850 to communicate through network 810 with the remote, distributed user devices. Database 870 may house an operating system 872, memory 874, and programs 876.

In one embodiment of the invention, the system 800 includes a cloud-based network 810 for distributed communication via a wireless communication antenna 812 and processing by at least one mobile communication computing device 830. In another embodiment of the invention, the system 800 is a virtualized computing system capable of executing any or all aspects of software and/or application components presented herein on the computing devices 820, 830, 840. In certain aspects, the computer system 800 may be implemented using hardware or a combination of software and hardware, either in a dedicated computing device, or integrated into another entity, or distributed across multiple entities or computing devices.

By way of example, and not limitation, the computing devices 820, 830, 840 are intended to represent various forms of digital computers 820, 840, 850 and mobile devices 830, such as a server, blade server, mainframe, mobile phone, personal digital assistant (PDA), smartphone, desktop computer, netbook computer, tablet computer, workstation, laptop, and other similar computing devices. The components shown here, their connections and relationships, and their functions, are meant to be exemplary only, and are not meant to limit implementations of the invention described and/or claimed in this document In one embodiment, the computing device 820 includes components such as a processor 860, a system memory 862 having a random access memory (RAM) 864 and a read-only memory (ROM) 866, and a system bus 868 that couples the memory 862 to the processor 860. In another embodiment, the computing device 830 may additionally include components such as a storage device 890 for storing the operating system 892 and one or more application programs 894, a network interface unit 896, and/or an input/output controller 898. Each of the components may be coupled to each other through at least one bus 868. The input/output controller 898 may receive and process input from, or provide output to, a number of other devices 899, including, but not limited to, alphanumeric input devices, mice, electronic styluses, display units, touch screens, signal generation devices (e.g., speakers), or printers.

By way of example, and not limitation, the processor 860 may be a general-purpose microprocessor (e.g., a central processing unit (CPU)), a graphics processing unit (GPU), a microcontroller, a Digital Signal Processor (DSP), an Application Specific Integrated Circuit (ASIC), a Field Programmable Gate Array (FPGA), a Programmable Logic Device (PLD), a controller, a state machine, gated or transistor logic, discrete hardware components, or any other suitable entity or combinations thereof that can perform calculations, process instructions for execution, and/or other manipulations of information.

In another implementation, shown as 840 in FIG. 18, multiple processors 860 and/or multiple buses 868 may be used, as appropriate, along with multiple memories 862 of multiple types (e.g., a combination of a DSP and a microprocessor, a plurality of microprocessors, one or more microprocessors in conjunction with a DSP core).

Also, multiple computing devices may be connected, with each device providing portions of the necessary operations (e.g., a server bank, a group of blade servers, or a multi-processor system). Alternatively, some steps or methods may be performed by circuitry that is specific to a given function.

According to various embodiments, the computer system 800 may operate in a networked environment using logical connections to local and/or remote computing devices 820, 830, 840, 850 through a network 810. A computing device 830 may connect to a network 810 through a network interface unit 896 connected to a bus 868. Computing devices may communicate communication media through wired networks, direct-wired connections or wirelessly, such as acoustic, RF, or infrared, through an antenna 897 in communication with the network antenna 812 and the network interface unit 896, which may include digital signal processing circuitry when necessary. The network interface unit 896 may provide for communications under various modes or protocols.

In one or more exemplary aspects, the instructions may be implemented in hardware, software, firmware, or any combinations thereof. A computer readable medium may provide volatile or non-volatile storage for one or more sets of instructions, such as operating systems, data structures, program modules, applications, or other data embodying any one or more of the methodologies or functions described herein. The computer readable medium may include the memory 862, the processor 860, and/or the storage media 890 and may be a single medium or multiple media (e.g., a centralized or distributed computer system) that store the one or more sets of instructions 900. Non-transitory computer readable media includes all computer readable media, with the sole exception being a transitory, propagating signal per se. The instructions 900 may further be transmitted or received over the network 810 via the network interface unit 896 as communication media, which may include a modulated data signal such as a carrier wave or other transport mechanism and includes any delivery media. The term "modulated data signal" means a signal that has one or more of its characteristics changed or set in a manner as to encode information in the signal.

Storage devices 890 and memory 862 include, but are not limited to, volatile and non-volatile media such as cache, RAM, ROM, EPROM, EEPROM, FLASH memory, or other solid state memory technology; discs (e.g., digital versatile discs (DVD), HD-DVD, BLU-RAY, compact disc (CD), or CD-ROM) or other optical storage; magnetic cassettes, magnetic tape, magnetic disk storage, floppy disks, or other magnetic storage devices; or any other medium that can be used to store the computer readable instructions and which can be accessed by the computer system 800.

It is also contemplated that the computer system 800 may not include all of the components shown in FIG. 18, may include other components that are not explicitly shown in FIG. 18, or may utilize an architecture completely different than that shown in FIG. 18. The various illustrative logical blocks, modules, elements, circuits, and algorithms described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application (e.g., arranged in a different order or partitioned in a different way), but such implementation decisions should not be interpreted as causing a departure from the scope of the present invention.

The above-mentioned examples are provided to serve the purpose of clarifying the aspects of the invention, and it will be apparent to one skilled in the art that they do not serve to limit the scope of the invention. The above-mentioned examples are just some of the many configurations that the mentioned components can take on. All modifications and improvements have been deleted herein for the sake of conciseness and readability but are properly within the scope of the present invention.

The invention claimed is:

1. A system for exchanging health data including a phenotype network comprising:
   at least one user device and at least one remote server in network communication with a health data exchange platform;
   wherein the at least one remote server includes a phenotype database, a report database, a recommendation database, and a permissions database;
   wherein the report database includes health data;
   wherein the at least one user device is operable to authorize sharing of selected health data with a third-party device via a graphical user interface (GUI), thereby creating selected permissible data;
   wherein the health data exchange platform is operable to exchange the selected permissible data with the third-party device;
   wherein the phenotype network includes a plurality of user nodes, a plurality of phenotype or concept nodes, a plurality of edges connecting the plurality of user nodes and/or the phenotype or concept nodes, and a user attribute inference module;
   wherein the user attribute inference module is operable to identify that an unknown, incomplete, and/or inaccurate user attribute for a particular user is present, determine an inferred user attribute corresponding to the unknown, incomplete, and/or inaccurate user attribute, and determine an inferred user attribute confidence value;
   wherein the phenotype network is operable to automatically suggest a connection with another user, at least one phenotype, at least one medical entity, and/or at least one health status;
   wherein the health data exchange platform receives a request from the at least one user device to generate a requested phenotype network based on one or more designated criteria; and
   wherein the health data exchange platform automatically generates the requested phenotype network and automatically excludes individual nodes from the phenotype network based on correlating criteria-specific data exclusions associated with each node with the one or more designated criteria.

2. The system of claim 1, wherein the at least one remote server includes a plurality of distributed servers.

3. The system of claim 2, wherein the health data exchange platform includes a distributed ledger, and wherein the health data exchange platform uses a private key and a public key to encrypt data stored on the distributed ledger.

4. The system of claim 1, wherein the permissions database stores information relating to what data each user has authorized to release to other entities.

5. The system of claim 1, wherein the phenotype database further includes a user profile database, and wherein the user profile database includes purchase history, social media history, web browsing history, biodata, sleep data, stress information, medications, supplements, disease profile, genotypes, workout information, diet information, social behaviors, emotional data, cognitive pursuits, data from third-party health applications, a frequency of interaction by the user with the phenotype network, hobbies, group memberships, and/or interests.

6. The system of claim 1, wherein the health data includes medical reports, sleep logs, wearable sensor data, blood test results, and/or genetic testing data.

7. The system of claim 1, further including a geographic database, wherein the geographic database includes information regarding known health issues by neighborhood, city, county, state, country, region, and/or zip code.

8. The system of claim 1, further including a medical community database, wherein the medical community database includes research studies, clinical trials, and/or disease information.

9. The system of claim 1, further including a plurality of prediction modules to determine an unknown, incomplete, and/or inaccurate user attribute.

10. The system of claim 9, wherein the unknown, incomplete, and/or inaccurate user attribute is determined using at least one decision tree, a random forest classifier, a binary classifier, a multiclass classifier, a linear classifier, a Naïve Bayesian classifier, a neural network, a Hidden Markov model, or a support vector machine.

11. The system of claim 1, further including a candidate connection generator, a conversion prediction engine, a value computation engine, an expected value scoring engine, and expected value rankings, and wherein the candidate connection generator, the conversion prediction engine, the value computation engine, the expected value scoring engine, and the expected value rankings are operable to automatically suggest the connection.

12. The system of claim 1, wherein the phenotype network system is operable to dynamically make recommendations based on social interactions, location data, biometric data, a digital footprint, and/or usage of the at least one user device.

13. The system of claim 1, wherein the health data exchange platform includes an action log, and wherein the action log records a timestamp of when an action occurred, an identification of a user, an action type, an identification of where the action was directed, and content associated with the action.

14. A system for exchanging health data including a phenotype network comprising:
   at least one user device and at least one remote server in network communication with a health data exchange platform;
   wherein the at least one remote server includes a phenotype database, a report database, a recommendation database, and a permissions database;
   wherein the report database includes health data;
   wherein the at least one user device is operable to authorize sharing of selected health data with a third-party device via a graphical user interface (GUI), thereby creating selected permissible data;
   wherein the health data exchange platform is operable to exchange the selected permissible data with the third-party device;
   wherein the phenotype network includes a plurality of user nodes, a plurality of phenotype or concept nodes, a plurality of edges connecting the plurality of user nodes and/or the phenotype or concept nodes, and a user attribute inference module;
   wherein the user attribute inference module is operable to identify that an unknown, incomplete, and/or inaccurate user attribute for a particular user is present, determine an inferred user attribute corresponding to the unknown, incomplete, and/or inaccurate user attribute, and determine an inferred user attribute confidence value;

wherein the phenotype network is operable to automatically suggest a connection with another user, at least one phenotype, at least one medical entity, and/or at least one health status;

wherein the health data exchange platform receives a request from the at least one user device to generate a requested phenotype network based on one or more designated criteria;

wherein the health data exchange platform automatically generates the requested phenotype network and automatically excludes individual nodes from the phenotype network based on correlating criteria-specific data exclusions associated with each node with the one or more designated criteria;

wherein the at least one remote server includes a plurality of distributed servers;

wherein the health data exchange platform includes a distributed ledger; and wherein the health data exchange platform uses a public key and a private key to encrypt data stored on the distributed ledger.

15. The system of claim 14, wherein the health data exchange platform is operable to execute a smart contract granting the third-party device access to the selected permissible data.

16. The system of claim 14, wherein the health data exchange platform is operable to process a micropayment between the at least one user device and the third-party device.

17. The system of claim 14, wherein the health data is stored off-chain.

18. The system of claim 14, wherein the health data exchange platform is built on an Ethereum blockchain or a Bitcoin blockchain.

19. The system of claim 14, wherein the permissions database stores links to one or more locations where the selected permissible data is stored on the distributed ledger.

20. A system for exchanging health data including a phenotype network comprising:

at least one user device and at least one remote server in network communication with a health data exchange platform;

wherein the at least one remote server includes a phenotype database, a report database, a recommendation database, and a permissions database;

wherein the report database includes health data;

wherein the at least one user device is operable to authorize sharing of selected health data with a third-party device via a graphical user interface (GUI), thereby creating selected permissible data;

wherein the health data exchange platform is operable to exchange the selected permissible data with the third-party device;

wherein the health data exchange platform is operable to process a micropayment between the at least one user device and the third-party device;

wherein the phenotype network includes a plurality of user nodes, a plurality of phenotype or concept nodes, a plurality of edges connecting the plurality of user nodes and/or the phenotype or concept nodes, and a user attribute inference module;

wherein the user attribute inference module is operable to identify that an unknown, incomplete, and/or inaccurate user attribute for a particular user is present, determine an inferred user attribute corresponding to the unknown, incomplete, and/or inaccurate user attribute, and determine an inferred user attribute confidence value;

wherein the phenotype network is operable to automatically suggest a connection with another user, at least one phenotype, at least one medical entity, and/or at least one health status;

wherein the health data exchange platform receives a request from the at least one user device to generate a requested phenotype network based on one or more designated criteria;

wherein the health data exchange platform automatically generates the requested phenotype network and automatically excludes individual nodes from the phenotype network based on correlating criteria-specific data exclusions associated with each node with the one or more designated criteria wherein the at least one remote server includes a plurality of distributed servers;

wherein the health data exchange platform includes a distributed ledger;

wherein the health data exchange platform uses a public key and a private key to encrypt data stored on the distributed ledger; and wherein the permissions database stores links to one or more locations where the selected permissible data is stored on the distributed ledger.

* * * * *